(12) United States Patent
Keane et al.

(10) Patent No.: US 9,212,214 B2
(45) Date of Patent: Dec. 15, 2015

(54) METHODS OF INCREASING THE EXPRESSION YIELD OF VITAMIN K-DEPENDENT PROTEINS

(75) Inventors: Julian Keane, Kingsville (AU); Anthony Stowers, Preston (AU); Peter Soupourmas, Melbourne (AU); Fraser Goodwin, Greenvale (AU)

(73) Assignee: CSL Limited, Parkville, Victoria (AU)

( * ) Notice: Subject to any disclaimer, the term of this patent is extended or adjusted under 35 U.S.C. 154(b) by 786 days.

(21) Appl. No.: 13/382,933

(22) PCT Filed: Jul. 9, 2010

(86) PCT No.: PCT/AU2010/000881
§ 371 (c)(1),
(2), (4) Date: Aug. 17, 2012

(87) PCT Pub. No.: WO2011/003153
PCT Pub. Date: Jan. 13, 2011

(65) Prior Publication Data
US 2012/0322107 A1    Dec. 20, 2012

Related U.S. Application Data

(60) Provisional application No. 61/237,016, filed on Aug. 26, 2009.

(30) Foreign Application Priority Data

Jul. 10, 2009  (EP) ..................................... 09009064

(51) Int. Cl.
| | |
|---|---|
| *C12N 5/00* | (2006.01) |
| *C12N 5/02* | (2006.01) |
| *C12N 5/07* | (2010.01) |
| *C07K 14/745* | (2006.01) |
| *C07K 14/78* | (2006.01) |
| *C12N 1/38* | (2006.01) |

(52) U.S. Cl.
CPC ............... *C07K 14/745* (2013.01); *C07K 14/78* (2013.01); *C12N 1/38* (2013.01); *C12N 5/0037* (2013.01); *C12N 2500/38* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 4,770,999 A * | 9/1988 | Kaufman et al. ............ 435/69.6 |
| 5,268,275 A | 12/1993 | Stafford et al. | |
| 5,714,583 A | 2/1998 | Foster et al. | |

FOREIGN PATENT DOCUMENTS

| | | |
|---|---|---|
| WO | 93/11225 | 6/1993 |
| WO | 00/54787 | 9/2000 |
| WO | 2005/030039 A2 | 4/2005 |
| WO | 2005/030039 A3 | 4/2005 |
| WO | 2005/040367 A1 | 5/2005 |
| WO | 2006/089613 A1 | 8/2006 |
| WO | 2006/101474 A1 | 9/2006 |
| WO | 2007/065173 A2 | 6/2007 |
| WO | 2007/065173 A3 | 6/2007 |
| WO | 2007/075976 A2 | 7/2007 |
| WO | 2007/075976 A3 | 7/2007 |

OTHER PUBLICATIONS

IARC Summaries & Evaluations Vitamin K Substances 2000 vol. 76: p. 417 (6 pages total).*
Benton, M.E., et al. 1995 Biochemistry 34: 9541-9551.*
Beck, R.,et al. 2009 Internation Journal of Toxicology 28(1): 33-42.*
PCT/AU2010/000881, International Search Report, mailed Sep. 8, 2010, 3 pp.
PCT/AU2010/000881, Written Opinion, mailed Sep. 8, 2010, 4 pp.
EP 09009064, Search Report with Annex, date completed Oct. 13, 2009, 6 pp.
Bettini et al., Book Review of "Handbook of Pharmaceutical Excipients" Third Ed., Kibbe (ed.) 2000, in Journal of Controlled Release, vol. 71, pp. 352-353 (2001).
Buitenhuis et al., "Comparison of the vitamins K1, K2 and K3 as cofactors for the hepatic vitamin K-dependent carboxylase" Biochimica et Biophysica Acta, vol. 1034, pp. 170-175 (1990).
Graham et al., "Characteristics of a Human Cell Line Transformed by DNA from Human Adenovirus Type 5" J. Gen. Virol., vol. 36, pp. 59-72 (1977).
Hallgren et al., "r-VKORC1 Expression in Factor IX BHK Cells Increases the Extent of Factor IX Carboxylation but is Limited by Saturation of Another Carboxylation Component or by a Shift in the Rate-Limiting Step" Biochemistry, vol. 45, pp. 5587-5598 (2006).
Isaacs et al., "A mechanistic study of the reduction of quinones by ascorbic acid" J Chem. Soc., Perkin Trans. 2, pp. 1465-1467 (1997).
Kaufman et al., "Expression, Purification, and Characterization of Recombinant gamma-Carboxylated Factor IX Synthesized in Chinese Hamster Ovary Cells" The Journal of Biological Chemistry, vol. 261, No. 21, pp. 9622-9628 (Jul. 25, 1986).
Lee, Book Review of "Pharmaceutical Formulation Development of Peptides and Proteins" Frokjaer et al., 2000, in European Journal of Pharmaceutics and Biopharmaceutics, vol. 50, pp. 329 (2000).
Rehemtulla et al., "In vitro and in vivo functional characterization of bovine vitamin K-dependent gamma-carboxylase expressed in Chinese hamster ovary cells" PNAS, vol. 90, pp. 4611-4615 (May 1993).

(Continued)

*Primary Examiner* — Marsha Tsay
(74) *Attorney, Agent, or Firm* — Calfee, Halter & Griswold LLP; Harry J. Guttman

(57) ABSTRACT

The invention encompasses the use of one or more compounds selected from a list comprising i) reduced forms of vitamin K and/or ii) reduced forms of a vitamin K analog and/or iii) reduced forms of a vitamin K precursor for the expression of one or more functional vitamin K-dependent proteins in cell culture as well as processes for the fermentation of eucaryotic cells expressing one or more vitamin K-dependent proteins wherein one or more compounds selected from a list comprising i) reduced forms of vitamin K and/or ii) reduced forms of a vitamin K analog and/or iii) reduced forms of a vitamin K precursor are added to the cell culture medium before and/or during the fermentation process.

17 Claims, 8 Drawing Sheets

(56) References Cited

OTHER PUBLICATIONS

Rost et al., "Mutations in VKORC1 cause warfarin resistance and multiple coagulation factor deficiency type 2" Nature, vol. 427, pp. 537-541 (Feb. 5, 2004).

Sadowski et at, "Vitamin K-dependent Carboxylase" The Journal of Biological Chemistry, vol. 251, No. 9, pp. 2770-2776 (May 10, 1976).

Stafford, "The Vitamin K Cycle" J. Thromb. Haemost, vol. 3, pp. 1873-1878 (2005).

Suhara et al., "Comparative uptake, metabolism, and utilization of menaquinone-4 and phylloquinone in human cultured cell lines" Bioorganic & Medicinal Chemistry, vol. 14, pp. 6601-6607 (2006).

Suhara et al., "Design and synthesis of biologically active analogues of vitamin K2: Evaluation of their biological activities with cultured human cell lines" Bioorganic & Medicinal Chemistry, vol. 16, pp. 3108-3117 (2008).

Urlaub et al., "Isolation of Chinese hamster cell mutants deficient in dihydrofolate reductase activity" PNAS, vol. 77, No. 7, pp. 4216-4220 (Jul. 1980).

Urlaub et al., "Deletion of the Diploid Dihydrofolate Reductase Locus from Cultured Mammalian Cells" Cell, vol. 33, pp. 405-412 (Jun. 1983).

Urlaub et al., "Effect of Gamma Rays at the Dihydrofolate Reductase Locus: Deletions and Inversions" Somatic Cell and Molecular Genetics, vol. 12, No. 6, pp. 555-566 (1986).

Wajih et al., "Engineering of a Recombinant Vitamin K-dependent gamma-Carboxylation System with Enhanced gamma-Carboxyglutamic Acid Forming Capacity" The Journal of Biological Chemistry, vol. 280, No. 11, pp. 10540-10547 (Mar. 18, 2005).

Wajih et al., "Increased Production of Functional Recombinant Human Clotting Factor IX by Baby Hamster Kidney Cells Engineered to Overexpress VKORC1, The Vitamin K 2,3-Epoxide-reducing Enzyme of the Vitamin K Cycle" The Journal of Biological Chemistry, vol. 280, No. 36, pp. 31603-31607 (Sep. 9, 2005).

Wajih et al., "Enhanced functional recombinant factor VII production by HEK 293 cells stably transfected with VKORC1 where the gamma-carboxylase inhibitor calumenin is stably suppressed by shRNA transfection" Thrombosis Research, vol. 122, pp. 405-410 (2008).

Weimer et al., "Prolonged in-vivo half-life of factor VIIa by fusion to albumin" Thromb. Haemost., vol. 99, pp. 659-667 (2008).

Wikipedia article, "Vitamin K" at web address <<http://en.wikipedia.org/wiki/Vitamin_K>>, last accessed Aug. 16, 2012.

English-language translation of Office Action in CN Application No. 201080030939.2 mailed May 7, 2014, 4 pages.

Office Action in CN Application No. 201080030939.2 mailed May 7, 2014, 3 pages.

Notice of Reasons for Rejection in JP Application No. 2012-518696 mailed Oct. 28, 2014, 5 pages.

English-language translation of Notice of Reasons for Rejection in JP Application No. 2012-518696 mailed Oct. 28, 2014, 7 pages.

\* cited by examiner

Figure 1: Vitamin K-dependent carboxylation of precursor factor IX
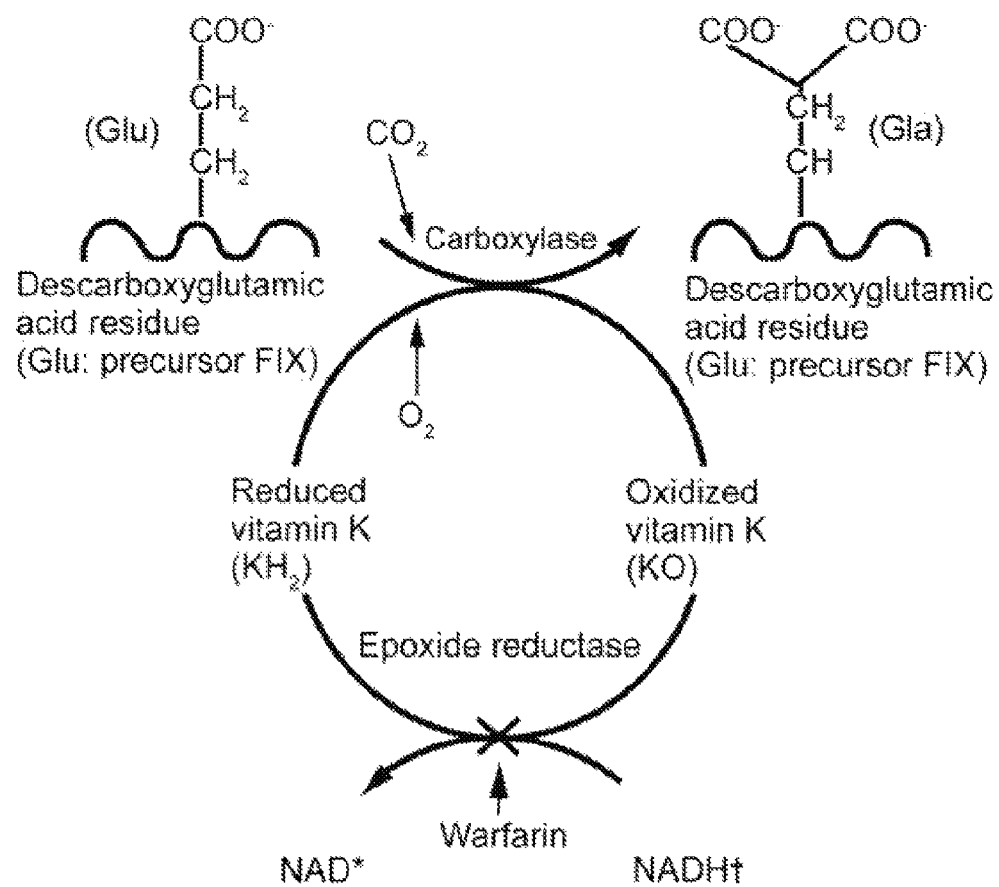

Figure 2: Chemical formulae of vitamin K1, K2 and menadione
Vitamin K1 (Phylloquinone)
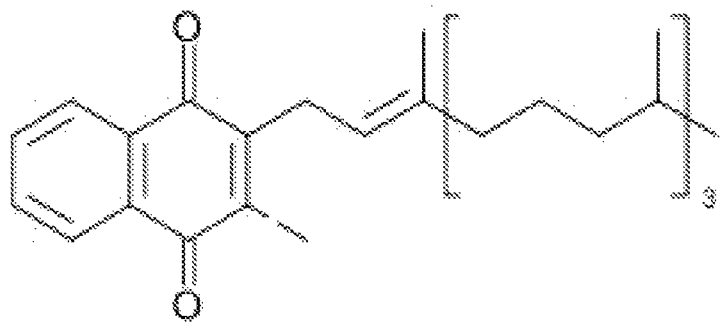
Vitamins K2 (menaquinones) with variable numbers (n)
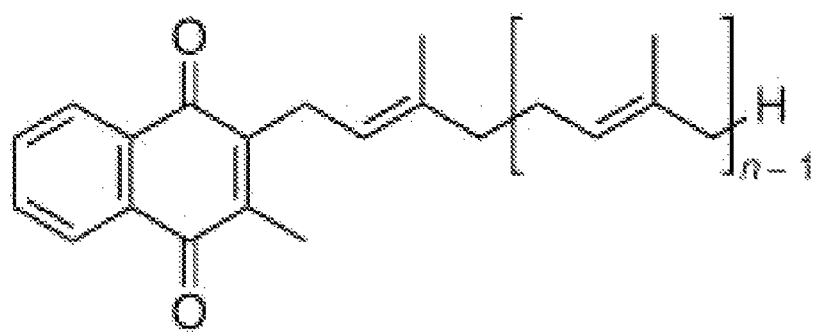
Menadione
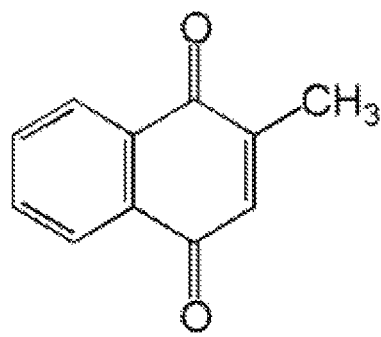

Figure 3: Reduction of menadione sodium bisulphite
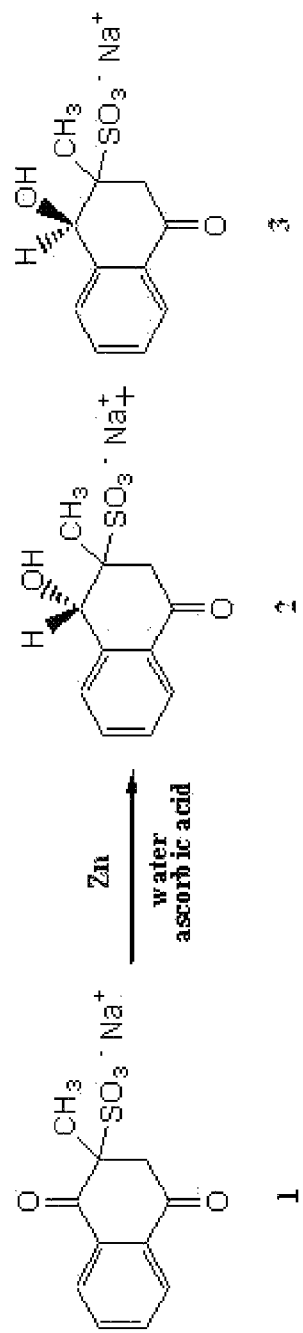

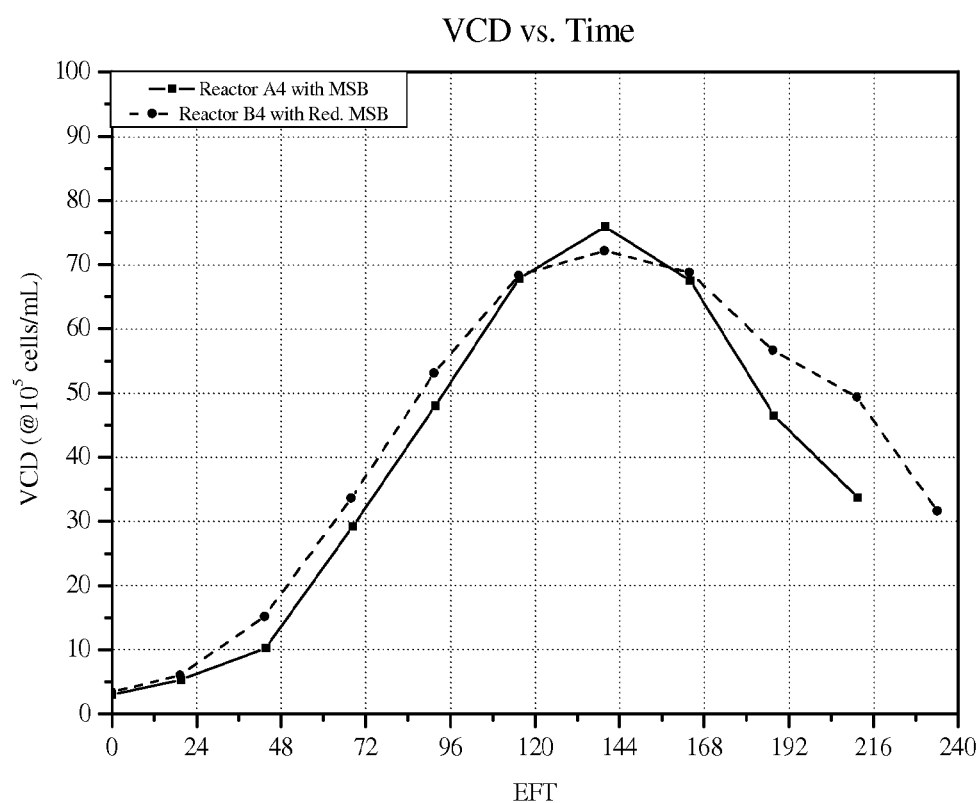
Figure 4: Total viable cell numbers plot for reactor A4 and B4 in Experiment 2

Figure 5: Viable cell density plot of the four reactors in Experiment 3
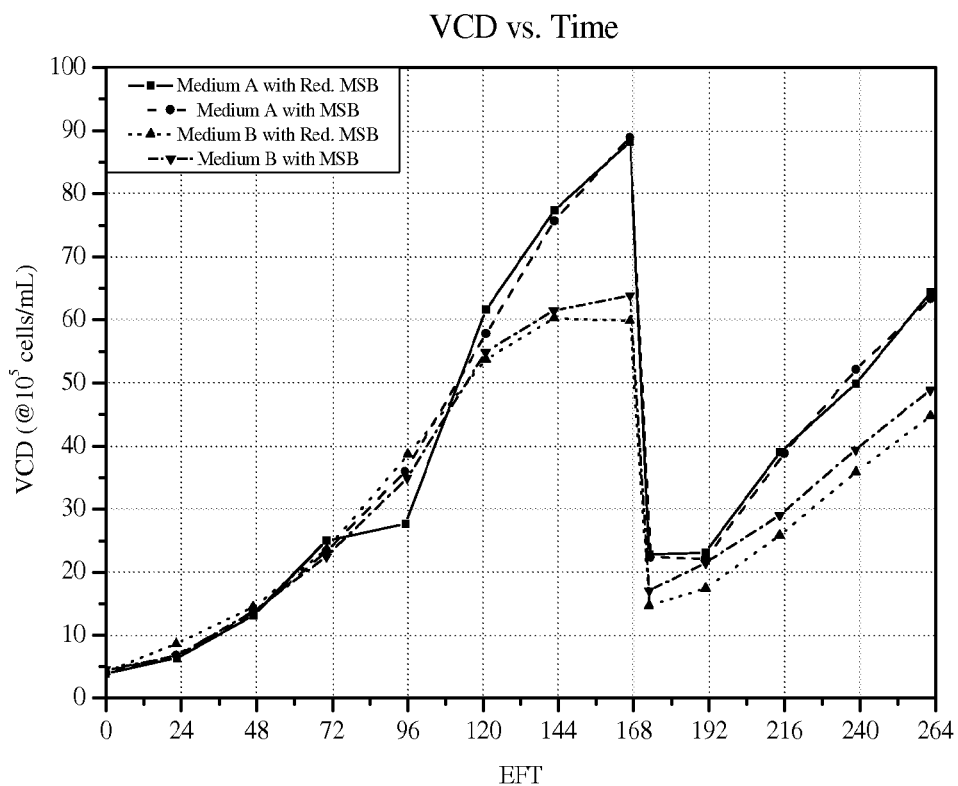

Figure 6: Viability of cells over time under increasing titration of MSB and rMSB
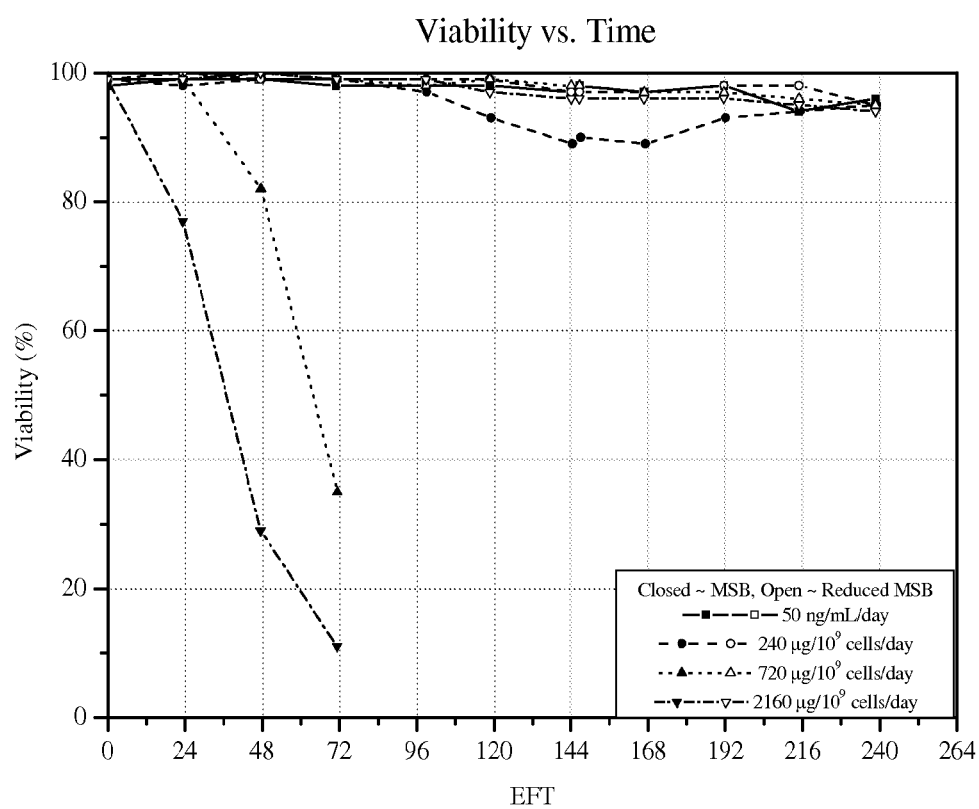

Figure 7: Viable cell density data under increasing titration of MSB and reduced MSB
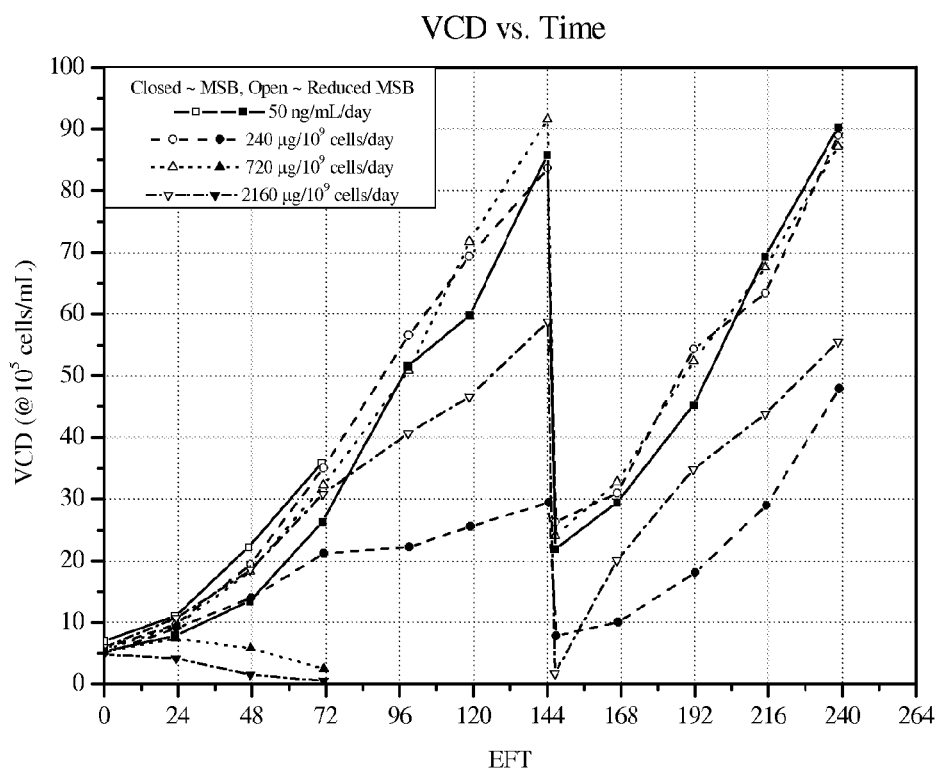

Figure 8:
a)
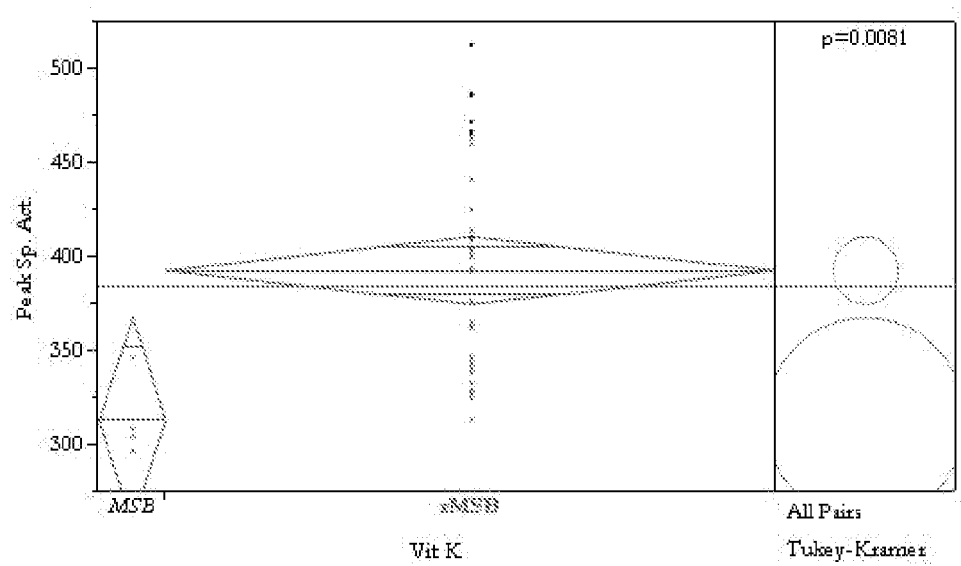
b)
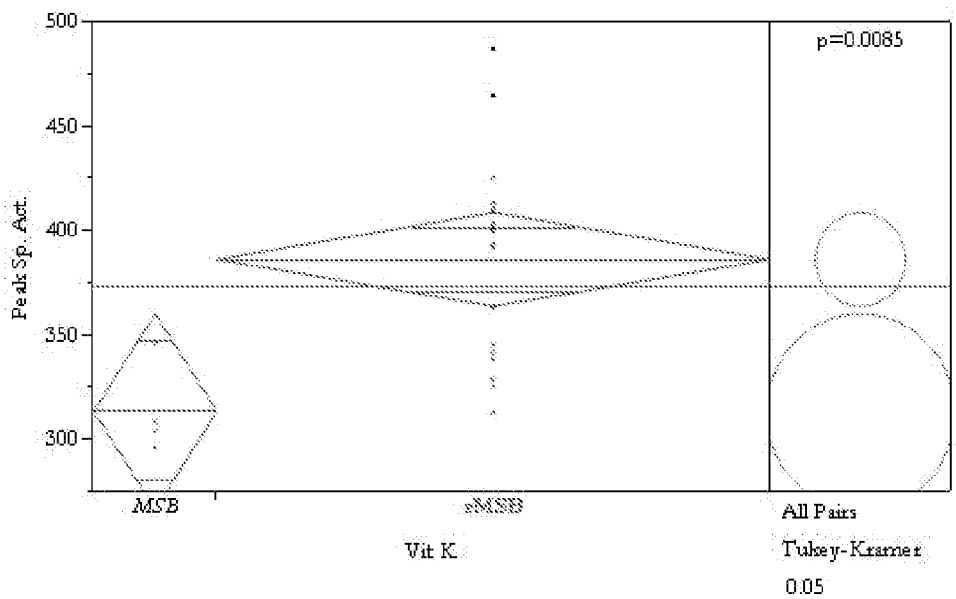

METHODS OF INCREASING THE EXPRESSION YIELD OF VITAMIN K-DEPENDENT PROTEINS

CROSS-REFERENCE TO RELATED APPLICATIONS

This application is a National Stage Entry of International Application No. PCT/AU2010/000881 filed Jul. 9, 2010, which is herein incorporated by reference in its entirety, which claims the benefit of U.S. Provisional Application No. 61/237,016, filed Aug. 26, 2009, which is herein incorporated by reference in its entirety, and which also claims priority to EP Application No. 09009064.8, filed Jul. 10, 2009, which is herein incorporated by reference in its entirety.

Vitamin K is involved in the carboxylation of certain glutamic acid residues in proteins to form gamma-carboxyglutamate residues (Gla-residues). The modified residues are located within specific protein domains called Gla domains. Gla-residues are usually involved in calcium binding. The Gla-residues are essential for the biological activity of all known Gla-proteins.

The biochemistry of how vitamin K is used to convert Glu to Gla has been elucidated over the past thirty years. Within the cell, vitamin K undergoes electron reduction to a reduced form of vitamin K (called vitamin K hydroquinone) by the enzyme vitamin K epoxide reductase (VKOR). The gene encoding VKOR (VKORC1) was identified recently, and is described in detail in Rost et al, 2004 ((2004) Nature, 427, 537-541)). Another enzyme then oxidizes vitamin K hydroquinone to allow carboxylation of Glu to Gla; this enzyme is called the gamma-glutamyl carboxylase or the vitamin K-dependent carboxylase (VKGC). The carboxylation reaction will only proceed if the carboxylase enzyme is able to oxidize vitamin K hydroquinone to vitamin K epoxide at the same time; the carboxylation and epoxidation reactions are said to be coupled reactions. Vitamin K epoxide is then re-converted to vitamin K by the vitamin K epoxide reductase. These two enzymes comprise the so-called vitamin K cycle.http://en.wikipedia.org/wiki/Vitamin_K cite note-Stafford-28#cite note-Stafford-28

At present, the following human Gla-containing proteins have been characterized to the level of primary structure: the blood coagulation factors II (prothrombin), VII, IX, and X, the anticoagulant proteins C and S, and the Factor X-targeting protein Z as well as the bone Gla-protein osteocalcin, the calcification inhibiting matrix Gla protein (MGP), the cell growth regulating growth arrest specific gene 6 protein (Gas6), and the four transmembrane Gla proteins (TMGPs) of yet unknown function. Gas6 can function as a growth factor that activates the Axl receptor tyrosine kinase and stimulates cell proliferation or prevents apoptosis in some cells. In all cases in which their function was known, the presence of the Gla-residues in these proteins turned out to be essential for functional activity. The multiple Gla residues allow the Gla-domain to undergo conformational changes which are required for the activity of vitamin K-dependent proteins in combination with binding to phospholipid membrane surfaces.

The vitamin K-dependent blood coagulation proteins require full or nearly full carboxylation to bind to membrane surfaces in the presence of calcium ions. If vitamin K antagonists inhibit gamma carboxylation, thus undercarboxylated vitamin K-dependent proteins cannot form the calcium dependent structure which results in low affinity to phospholipids membranes and less activity. Missing procoagulant activity of undercarboxylated Factor IX mutants found in hemophilia B patients can be assigned to impaired calcium-induced conformational changes and loss in the ability to bind phospholipid vesicles.

Biotechnology has offered the promise of producing low cost biopharmaceutical products. Regarding coagulation factors this offered the chance to provide a wider range of hemophiliacs with adequate treatment. Unfortunately, this promise has not been met due in major part to the inherent complexity of naturally occurring biological molecules and a variety of limitations associated with the synthesis of their recombinant protein counterparts in genetically engineered cells.

The present application addresses a need for a method to produce vitamin K-dependent proteins such as Factor IX or Factor VII/VIIa which have been properly processed so that they are active and in sufficient yield for commercial production. To increase the availability of vitamin K-dependent blood coagulation proteins to meet the worldwide medical need for the treatment of bleeding disorders such as hemophilia B, improvements in the production of fully functional protein, Factor IX in this example, from genetically engineered cells are required. Specifically, identification and supplementation of deficiencies in the enzymatic activities required to obtain essentially complete post-translational modification are needed.

Therefore a strong need exists for enhancing the expression, particularly the recombinant expression of vitamin K-dependent proteins in host organisms yielding in improved secretion rates and/or activities of the expressed vitamin K-dependent proteins. Recombinant over-expression of gamma-carboxylated proteins was shown in case of human Factor IX to lead to a limitation of propeptide cleavage and gamma-carboxylation at higher secretion rates, thus yielding proteins which are only partially occupied with Gla residues also when vitamin K is available in the culture medium in surplus. This leads to the secretion of variants of vitamin K-dependent recombinant proteins with reduced activities. Addition of vitamin K to the medium did not improve Factor IX activity at high expression levels. The requirement of vitamin K present in the cell culture medium to elicit active Factor IX was shown to reach saturation at 5 µg/ml. Below this level, the secreted amount of active Factor IX from Chinese hamster ovary (CHO) cells was dependent on vitamin K concentration (Kaufman, R. J. et al. (1986), J. Biol. Chem., 261, 9622-9628).

Vitamin K and vitamin K analogs comprise a group of lipophilic, hydrophobic vitamins that possess a common 2-methyl-1,4-naphthoquinone structure, called menadione.

All members of the vitamin K group of vitamins share a methylated naphthoquinone ring structure, and vary in the aliphatic side chain attached at the 3-position.

Plants and cyanobacteria, almost invariably, synthesize only one chemical form called phylloquinone (also known as vitamin $K_1$) which has the same phytyl side chain as in chlorophyll.

Menaquinones (Also Known As Vitamins $K_2$) Normally Produced By Bacteria In The Intestines, Differ From Phylloquinone In That The 3-Side Chain Comprises, For The Most Part, A Polymer Of Repeating Prenyl Units Rather Than The Phytyl Chain. For Purposes Of Nomenclature The Menaquinones Are Classified According To The Number Of Prenyl Units, This Number Being Given As A Suffix (I.E. Menquinone-N Abbreviated Mk-N) Some Of The Prenyl Units Can Also Be Saturated Indicated By The Prefix Dihydro-, Tetrahydro, And So Forth And Are Abbreviated Mk-N (H2), Mk-N(H4) Etc.

It is generally accepted that the naphthoquinone is the functional group, so that the mechanism of action is similar for all K-vitamins. It was also shown in a cell free system that menadione and reduced menadione are inactive in promoting gamma carboxylation (Sadowski et al. (1976), J. Biol. Chem. Vol. 251, No. 9 pp. 2770-2776).

In addition to supplementing vitamin K to the cell culture medium other means to enhance the expression of functional vitamin K have been tried.

The overexpression of vitamin K-dependent gamma-carboxylase (VKGC), has not led to improved protein secretion in case of Factor IX (Rehemtulla, A. et al. (1993) PNAS 90, 4611-4615).

Recently some groups showed that the co-expression of both VKGC and VKOR can increase the expression level of functional vitamin K-dependent proteins (WO 2005/030039, WO 2005/040367, WO 2006/089613, WO 2006/101474, WO 2007/065173 and WO 2007/075976).

SUMMARY OF THE INVENTION

The inventors of the present invention have surprisingly found that by supplementing cell culture media of vitamin K-dependent proteins with one or more compounds selected from a list comprising i) reduced forms of vitamin K and/or ii) reduced forms of a vitamin K analog and/or iii) reduced forms of a vitamin K precursor the expression yield of the respective active vitamin K-dependent protein can be significantly increased as compared to the expression yield which is obtained when the same amount of the same but non-reduced form of the respective vitamin K and/or the vitamin K analog and/or the vitamin K precursor is added to the cell culture medium.

One embodiment of the invention is the use of a reduced form of vitamin K and/or a reduced form of a vitamin K analog protein to enhance the expression yield of a functional vitamin K-dependent protein in mammalian cells.

Other embodiments of the invention are directed to methods of producing a recombinant biologically active vitamin K-dependent protein product, which comprises using a mammalian cell with at least one gene encoding a vitamin K-dependent protein operably linked to a promoter expressing said biologically active vitamin K-dependent protein in a cell culture medium which comprises at least at some point in time during the expression phase a reduced form of vitamin K and/or a reduced form of a vitamin K analog and/or a reduced form of a vitamin K precursor and harvesting the vitamin K-dependent protein product. Optionally the mammalian cell line comprises in addition at least one gene encoding a processing factor operably linked to at least one promoter. In preferred embodiments, the vitamin K-dependent protein product is Factor II, Factor VII, Factor IX, Factor X, Protein C or Protein S. More preferably, the vitamin K-dependent protein is Factor IX or Factor VII.

In preferred embodiments, the processing factor is a nucleic acid selected from paired basic amino acid converting enzyme (PACE), vitamin K-dependent epoxide reductase (VKOR), vitamin K-dependent gamma-glutamyl carboxylase (VKGC) and combinations thereof operably linked to one or more promoters. More preferably, the processing factor proteins include VKOR and VKGC. Preferably, at least one of the genes is overexpressed.

The invention encompasses therefore the use of one or more compounds selected from a list comprising i) reduced forms of vitamin K and/or ii) reduced forms of a vitamin K analog and/or iii) reduced forms of a vitamin K precursor for the expression of one or more functional vitamin K-dependent proteins in cell culture as well as processes for the fermentation of eucaryotic cells expressing one or more vitamin K-dependent proteins wherein one or more compounds selected from a list comprising i) reduced forms of vitamin K and/or ii) reduced forms of a vitamin K analog and/or iii) reduced forms of a vitamin K precursor are added to the cell culture medium before and/or during the fermentation process.

The invention also encompasses the use of reduced forms of vitamin K and/or a vitamin K analog and/or a vitamin K precursor to enhance the viability of cells in fermentation.

BRIEF DESCRIPTION OF THE DRAWINGS

FIG. 1: Vitamin K-dependent carboxylation of precursor factor IX

FIG. 2: Chemical formulae of vitamin K1, K2 and menadione

FIG. 3: Reduction of menadione sodium bisulphite

FIG. 4: Total viable cell numbers plot for reactor A4 and B4 in Experiment 2

FIG. 5: Viable cell density plot of the four reactors in Experiment 3

FIG. 6: Viability of cells over time under increasing titration of MSB and rMSB

FIG. 7: Viable cell density data under increasing titration of MSB and rMSB

FIG. 8: (a) The influence of Factor VII activity of albumin-fused Factor VII when expressed in CHO-S cells cultivated with Menadione Sodium Bisulphite (MSB) compared to cultivation with reduced Menadione Sodium Bisulphite (rMSB). (b) The influence of Factor IX activity of albumin-fused Factor IX when expressed in CHO-S cells cultivated with Menadione Sodium Bisulphite (MSB) compared to cultivation with reduced Menadione Sodium Bisulphite (rMSB).

DETAILED DESCRIPTION

While the described embodiments represent the preferred embodiments of the present invention, it is to be understood that modifications will occur to those skilled in the art without departing from the gist of the invention. The scope of the invention is therefore to be determined solely by the appended claims.

Preferred embodiments of the invention are directed to the use of a reduced form of vitamin K and/or a reduced form of a vitamin K analog and/or a reduced form of a vitamin K precursor for increasing the expression yield of a functional vitamin K-dependent protein in cell culture. The reduced form of vitamin K and/or a reduced form of a vitamin K analog and/or a reduced form of a vitamin K precursor is added to the cell culture medium, where it its taken up by the cells.

Preferably water soluble reduced forms of vitamin K and/or a reduced forms of a vitamin K analog and/or a reduced forms of a vitamin K precursor are used. However by way of endocytosis and/or specific receptors also water insoluble reduced forms of vitamin K and/or a reduced forms of a vitamin K analog and/or a reduced forms of a vitamin K precursor will be taken up by the cells.

One embodiment of the invention is directed to the use of a reduced form of vitamin K and/or a reduced form of a vitamin K analog and/or a reduced form of a vitamin K precursor for the expression of a functional vitamin K-dependent protein in cell culture, wherein the expression yield of the respective functional vitamin K-dependent protein is increased as compared to the expression yield which is obtained when the same amount of the same but non-reduced form of the respective vitamin K and/or the vitamin K analog and/or the vitamin K precursor is added to the cell culture medium in the same manner. Preferred embodiments of the invention are directed to methods for enhancing the yield of biologically active vitamin K-dependent proteins in mammalian cells. Preferentially the cells are genetically engineered.

Embodiments of the invention are described with respect to production of Factor IX and Factor VII. However, the disclosed methods are applicable to all vitamin K-dependent proteins: the blood coagulation factors II (prothrombin), VII, IX, and X, the anticoagulant proteins C and S, and the Factor X-targeting protein Z as well as the bone Gla-protein osteocalcin, the calcification inhibiting matrix Gla protein (MGP), the cell growth regulating growth arrest specific gene 6 protein (Gas6), and the four transmembrane Gla proteins (TMGPs).

In a preferred embodiment of the invention vitamin K-dependent proteins are expressed in a cell culture medium comprising reduced forms of vitamin K and/or reduced forms of vitamin K-analogs and/or reduced forms of vitamin K precursors at some point in time during the expression phase.

Vitamin K and vitamin K-analogs comprise a group of lipophilic, hydrophobic vitamins that possess a common 2-methyl-1,4-naphthoquinone structure, called menadione.

All members of the vitamin K group of vitamins share a methylated naphthoquinone ring structure, and vary in the aliphatic side chain attached at the 3-position.

Plants and cyanobacteria, almost invariably, synthesize only one chemical form called phylloquinone (also known as vitamin $K_1$) which has the same phytyl side chain as in chlorophyll.

Menaquinones (also known as vitamins K2) normally produced by bacteria in the intestines, differ from phylloquinone in that the 3-side chain comprises, for the most part, a polymer of repeating prenyl units rather than the phytyl chain. For purposes of nomenclature the menaquinones are classified according to the number of prenyl units, this number being given as a suffix (i.e. menquinone-n abbreviated MK-n) some of the prenyl units can also be saturated indicated by the prefix dihydro-, tetrahydro, and so forth and are abbreviated MK-n (H2), MK-n(H4) etc.

It is generally accepted that the naphthoquinone is the functional group, so that the mechanism of action is similar for all K-vitamins.

The relative ability for phylloquinone and several menaquinones to act as cofactors for VKGC was measured in a partially purified hepatic microsomal enzyme preparation (Buitenhuis et al., Biochim. Biophys Acta (1990) 1034:170-175). The activity of the menaquinones varied with 3-side chain length and decreased as the length increased.

As used herein the term "vitamin K" comprises a) vitamin K1 (phylloquinone, see FIG. 2) including its various salts like Vitamin K1 diphosphate (2-methyl-3-pyhtyl-1,4-naphtohydroquinone-1,4-diphosphate), Vitamin K1 diacetate (2-methyl-3-pyhtyl-1,4-naphtohydroquinone-1,4-diacetate) and Vitamin K1 disulfate: (2-methyl-3-pyhtyl-1,4-naphtohydroquinone-1,4-disulfate).

b) vitamins K2 (menaquinones, see FIG. 2) with variable numbers (n)

c) vitamin K analogs d) vitamin K precursors like menadione (see FIG. 2), menadiol diacetate (2-Methyl-1,4-naphthohydroquinone diacetate), menadiol diphosphate(Tetrasodium 2-methyl-1,4-naphthalenediol-bis(dihydrogen phosphate)hexahydrate), menadiol dibutyrate: (2-Methyl-1,4-naphthalenediol dibutyrate), menadiol disulphate: 2-methyl-1,4-naphthalenediol bis(hydrogen sulfate)disodium salt, menadione nicotinamide bisulfite (2-Methyl-1,4-naphthalenediol bis(hydrogen sulfate)disodium salt and menadoxime: (3-Methyl-4-oxo-1(4H)-naphthalenylidene)amino]oxy]-acetic acid ammonium salt.

As used herein "vitamin K analog" comprises any other chemical compound as long as the chemical compound comprises a 2-methyl-1,4-naphthoquinone ring structure and can functionally substitute for vitamin K1 in the vitamin-K cycle dependent gamma carboxylation of glutamic acid residues to Gla-residues in vitamin K-dependent proteins.

As used herein "vitamin K precursor" comprises any other chemical compound, which after having been taken up by a mammalian cell can be transformed by said mammalian cell to a chemical compound which comprises a methylated naphthoquinone ring structure, and can functionally substitute for vitamin K1 in the vitamin-K cycle dependent gamma carboxylation of glutamic acid residues to Gla-residues in vitamin K-dependent proteins, e.g. menadione.

As used herein "reduced form of vitamin K and/or a reduced form of a vitamin K analog and/or a reduced form of a vitamin K precursor" means any chemical compound, including the hydroquinone forms of the different forms of vitamin K, vitamin K analogs and vitamin K precursors as defined above, which is accepted without the need for a further reductive step as a co-substrate of VKGC in the carboxylation reaction transforming glutamic acid residues to Gla-residues in vitamin K-dependent proteins.

The reduced form of vitamin K and/or a reduced form of a vitamin K analog and/or a reduced form of a vitamin K precursor has to be present in the cell culture medium at some time during the expression phase of the vitamin K-dependent protein of interest. Encompassed by the invention methods to express a vitamin K-dependent protein in which cell culture media comprise a single reduced form of vitamin K or a single reduced form of a vitamin K analog or a single reduced form of a vitamin K precursor or more than one member of each of those classes of chemical compounds as well as combinations of one or more members of each class of those classes of chemical compounds.

One way to reduce quinones is by the action of zinc powder and zinc chloride or zinc powder and hydrogen ions.

Ascorbic acid at acidic pH, preferably at a pH between 2 and 4.5 (Isaacs et al. (1997) J. Chem. Soc. Perkin Trans. 2, page 1465 to 1467) is known to have a limited ability to reduce quinones.

One embodiment of the present invention is a novel way to produce rMSB by using zinc powder in combination with ascorbic acid at a pH of around 5.3 for the reduction of MSB by zinc. The ascorbic acid acts as a source of hydrogen ions and assists in keeping the rMSB in the reduced form.

Other embodiments of the invention are directed to methods and processes of producing a recombinant biologically active vitamin K-dependent protein product, which comprises using a mammalian cell with a gene encoding the vitamin K-dependent protein operably linked to a promoter expressing said biologically active vitamin K-dependent protein in a cell culture medium which comprises at least at some point in time during the expression phase a reduced form of vitamin K and/or a reduced form of a vitamin K analog and/or a reduced form of a vitamin K precursor protein and harvesting the vitamin K-dependent protein product. Optionally in addition the cell line comprises at least one gene encoding a processing factor operably linked to at least one promoter.

As used herein "functional" means that the vitamin K-dependent protein has preferably at least 10%, preferably at least 25% biological activity of the respective vitamin K-dependent protein when isolated from plasma. For example when expressing Factor IX its functionality is determined with reference to a Factor IX standard derived from human plasma, such as MONONINE® (CSL Behring). The biological activity of the respective vitamin K-dependent protein standard is taken to be 100%. The respective vitamin K-dependent protein has preferably at least 10% of the biologically activity of the respective vitamin K-dependent protein standard. Preferably, the respective vitamin K-dependent protein according to embodiments of the invention has at least 25% of the biological activity of the respective vitamin K-dependent protein standard, more preferably at least 50% of the biological activity of the respective vitamin K-dependent protein standard.

Another aspect of the invention is that by using reduced forms of vitamin K and/or a reduced form of a vitamin K analog and/or a reduced form of a vitamin K precursor in a method or process of the invention the ratio of the specific activity of the vitamin K-dependent protein over the antigen content of the vitamin K-dependent protein is preferably at least 15% or preferably at least 25%, or more preferably at least 50%, or even more preferably at least 75% or at least 100% increased as compared to the ratio of the specific activity of the vitamin K-dependent protein over the antigen content of the vitamin K-dependent protein of the same functional vitamin K-dependent protein which is obtained when the same amount of the same but non-reduced form of the respective vitamin K and/or the vitamin K analog and/or the vitamin K precursor is added to the cell culture medium in the same manner.

By way of non-limiting example the vitamin K-dependent protein Factor IX expressed according to the invention in the presence of reduced forms of vitamin K and/or a reduced form of a vitamin K analog and/or a reduced form of a vitamin K precursor has at least an activity/antigen ratio of 0.7, or preferably at least 1 or more preferably at least 1.5 or even more preferably at least 2.

Another aspect of the invention is that by using reduced forms of vitamin K and/or a reduced form of a vitamin K analog and/or a reduced form of a vitamin K precursor in a method or process of the invention the cell density specific activity productivity of the vitamin K-dependent protein is increased by at least 25% or preferably at least by 50%, or more preferably at least by 75% as compared to the cell density specific activity productivity of the same functional vitamin K-dependent protein which is obtained when the same amount of the same but non-reduced form of the respective vitamin K and/or the vitamin K analog and/or the vitamin K precursor is added to the cell culture medium in the same manner.

Also by way of non-limiting example the vitamin K-dependent protein Factor IX expressed according to the invention in the presence of reduced forms of vitamin K and/or a reduced form of a vitamin K analog and/or a reduced form of a vitamin K precursor has at least a cell specific activity productivity of 0.22 U/$10^6$ cells/day or preferably at least U/$10^6$ cells/day or at least 0.37 U/$10^6$ cells/day.

In some embodiments, gamma-carboxylation is increased by replacing the native propeptide sequence with a propeptide sequence that has a lower affinity for the gamma carboxylase as discussed in WO 00/54787, which is incorporated herein by reference. Useful propeptide sequences include altered forms of wild type sequences or propeptide sequences, or combinations of the same, for heterologous vitamin K-dependent proteins. The propeptide sequence in vitamin K-dependent proteins is the recognition element for the enzyme which directs gamma carboxylation of the protein. Vitamin K-dependent proteins are not fully functional unless they comprise a high percentage of gamma carboxylated moieties. Thus, it is important when generating recombinant versions of these proteins that mechanisms be put in place to ensure full gamma carboxylation of the same.

The sequence alignment of several propeptide sequences is shown in FIG. 3 of WO 00/54787. Thus, propeptides which are useful in the present invention are those which have the sequences shown in FIG. 3 wherein an 18 amino acid sequence of several useful propeptides is shown along with the relative affinities of these propeptides for gamma carboxylase. A low affinity propeptide may be generated by modifying any one of amino acids −9 or −13 on either prothrombin or protein C. Preferred modifications include the substitution of an Arg or a His residue at position −9 and the substitution of a Pro or a Ser residue at position −13. Other preferred chimeric proteins include a propeptide selected from the group consisting of altered Factor IX, Factor X, Factor VII, Protein S, Protein C and prothrombin, or an unaltered propeptide in combination with the mature vitamin K-dependent protein which is not native to the chosen propeptide sequence.

The term "processing factor" is a broad term which includes any protein, peptide, non-peptide cofactor, substrate or nucleic acid which promotes the formation of a functional vitamin K-dependent protein. Examples of such processing factors include, but are not limited to, PACE, VKOR and VKGC.

As used herein, the term "PACE" is an acronym for paired basic amino acid converting (or cleaving) enzyme. PACE, originally isolated from a human liver cell line, is a subtilisin-like endopeptidase, i.e., a propeptide-cleaving enzyme which exhibits specificity for cleavage at basic residues of a protein, e.g., -Lys-Arg-, -Arg-Arg, or -Lys-Lys-. The co-expression of PACE and a proprotein which requires processing for production of the mature protein results in high level expression of the mature protein. Additionally, co-expression of PACE with proteins requiring gamma-carboxylation for biological activity permits the expression of increased yields of functional, biologically active mature proteins in eukaryotic, preferably mammalian, cells.

Vitamin K-dependent epoxide reductase (VKOR) is important for vitamin K-dependent proteins because vitamin K is converted to vitamin K epoxide during reactions in which it is a cofactor. The amount of vitamin K in the human diet is limited. Therefore, vitamin K epoxide must be converted back to vitamin K by VKOR to prevent depletion. Consequently, co-transfection with VKOR provides sufficient vitamin K for proper functioning of the vitamin K-dependent enzymes such as the vitamin K-dependent gamma-glutamyl carboxylase (VKCG). Proper functioning of vitamin K-dependent VKCG is essential for proper gamma-carboxylation of the Gla-domain of vitamin K-dependent coagulation factors.

Vitamin K-dependent gamma-glutamyl carboxylase (VKGC) is an enzyme involved in the post-translation modification of vitamin K-dependent proteins. VKGC incorporates carboxy groups into glutamic acid to modify multiple residues within the vitamin K-dependent protein within about 40 residues of the propeptide. The cDNA sequence for human vitamin K-dependent gamma-glutamyl carboxylase is described by U.S. Pat. No. 5,268,275, which is incorporated herein by reference.

A vector is a DNA construct with an ability to replicate in a host, usually conferred by an origin of replication, and a selection gene to facilitate recognition of transformants. Vectors are used herein either to amplify DNA encoding vitamin K-dependent Proteins and/or to express DNA which encodes vitamin K-dependent Proteins. An expression vector is a replicable DNA construct in which a DNA sequence encoding a vitamin K-dependent protein is operably linked to suitable control sequences capable of effecting the expression of a vitamin K-dependent protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Vectors comprise plasmids, viruses (e.g., adenovirus, cytomegalovirus), phage, and DNA fragments which are able to integrate into the host genome by recombination. The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation. Transformed host cells are cells which have been transformed or transfected with one or more vectors comprising one or more genes coding for one or more vitamin K-dependent protein vector(s) a using recombinant DNA techniques.

Embodiments of the invention are directed to providing the cell with the necessary enzymes and cofactors to process vitamin K-dependent proteins so that higher yields of biologically active vitamin K-dependent proteins are achieved. When adequate levels of fully functional vitamin K-dependent proteins are produced by a recombinant cell, lengthy purification steps designed to remove the useless, partially modified, or unmodified vitamin K-dependent protein from the desired product are avoided. This lowers the production cost and eliminates inactive material that may have undesirable side effects for the patient.

In preferred embodiments, methods for producing vitamin K-dependent proteins by co-expression with PACE, VKGC and/or VKOR can include the following techniques. First, a single vector containing coding sequences for more than one protein such as PACE and a vitamin K-dependent protein can be inserted into a selected host cell. Alternatively, two or more separate vectors encoding a vitamin K-dependent protein plus one or more other proteins, can be inserted into a host. Upon culturing under suitable conditions for the selected host cell, the two or more proteins are produced and interact to provide cleavage and modification of the proprotein into the mature protein.

Another alternative is the use of two transformed host cells wherein one host cell expresses the vitamin K-dependent protein and the other host cell expresses one or more of PACE, VKGC and/or VKOR which will be secreted into the medium. These host cells can be co-cultured under conditions which allow expression and secretion or release of the recombinant vitamin K-dependent protein and the co-expressed recombinant proteins, including cleavage into the mature form by the extracellular PACE and gamma carboxylation of N-terminal glutamates. In this method, it is preferred that the PACE protein lacks the transmembrane domain so that it secretes into the medium.

In some instances, it may be desirable to have a plurality of copies, two or more, of the gene expressing the vitamin K-dependent protein in relation to the other genes, or vice versa. This can be achieved in a variety of ways. For example, one may use separate vectors or plasmids, where the vector containing the vitamin K-dependent protein encoding polynucleotide has a higher copy number than the vector containing the other polynucleotide sequences, or vice versa. In this situation, it would be desirable to have different selectable markers on the two plasmids, so as to ensure the continued maintenance of the plasmids in the host. Alternatively, one or both genes could be integrated into the host genome, and one of the genes could be associated with an amplifying gene, (e.g., dhfr or one of the metallothionein genes).

Alternatively, one could employ two transcriptional regulatory regions having different rates of transcriptional initiation, providing for the enhanced expression of either vitamin K-dependent protein or the expression of any of the other processing factor proteins, relative to vitamin K-dependent protein. As another alternative, one can use different promoters, where one promoter provides for a low level of constitutive expression of vitamin K-dependent protein, while the second promoter provides for a high level of or induced expression of the other products. A wide variety of promoters are known for the selected host cells, and can be readily selected and employed in the invention by one of skill in the art such as CMV, MMTV, SV 40 or SRa promoters which are well known mammalian promoters.

Production of biologically active vitamin K-dependent proteins such as Factor IX or Factor VII/VIIa, are optionally maximized by overexpression of one or more of PACE, VKOR, and/or VKGC and/or by modification of the Gla region to maximize gamma-carboxylation. That is, rate limiting components are expressed in sufficient quantity so that the entire system operates to produce a commercially viable quantity of vitamin K-dependent protein.

Suitable host cells include prokaryote, yeast or higher eukaryotic cells such as mammalian cells and insect cells. Cells derived from multicellular organisms are a particularly suitable host for recombinant vitamin K-dependent protein synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, Chinese hamster ovary (CHO) cell lines, and WI138, HEK 293, BHK, COS-7, Per.C6, HepG2, HeLa, Vero, COS, CV, and MDCK cell lines. A preferred cell line is CHO-K1 or CHO-S.

Expression vectors for such cells ordinarily include (if necessary) an origin of replication, a promoter located upstream from the DNA encoding vitamin K-dependent protein(s) to be expressed and operatively associated therewith, along with a ribosome binding site, an RNA splice site (if intron-containing genomic DNA is used), a polyadenylation site, and a transcriptional termination sequence.

An origin of replication may be provided either by construction of the vector to include an exogenous origin, such as may be derived from SV 40 or other viral (e.g. Polyoma, Adenovirus, VSV, or BPV) source, or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the DNA for the vitamin K-dependent protein(s). Examples of suitable selectable markers are dihydrofolate reductase (DHFR) or thymidine kinase.

In general if cells other than mammalian cells are used for the expression of vitamin K-dependent proteins, it might be necessary to provide also other genes coding for proteins essential for post-translational modifications required for the biological function of the proteins of interest.

Cloned genes of the present invention may code for any species of origin, including mouse, rat, rabbit, cat, porcine, and human, but preferably code for vitamin K-dependent proteins of human origin. DNA encoding vitamin K-dependent proteins that is hybridizable with DNA encoding for proteins disclosed herein is also encompassed.

Hybridization of such sequences may be carried out under conditions of reduced stringency or even stringent conditions (e.g., conditions represented by a wash stringency of 0.3M NaCl, 0.03M sodium citrate, 0.1% SDS at 60° C. or even 70° C. to DNA encoding the vitamin K-dependent protein disclosed herein in a standard in situ hybridization assay. See J. Sambrook et al., Molecular Cloning, A Laboratory Manual (2d Ed. 1989 Cold Spring Harbor Laboratory)).

referred processes for the expression of vitamin K-dependent proteins in cell culture are suspension cell culture processes of which there are the three main options: 1. perfusion processes and 2. batch processes and 3. draw-fill processes.

1. Perfusion Processes:

In a suspension cell-perfusion process the cells are inoculated into a seed culture vessel containing culture medium preferably lacking animal-derived components and propagated until the cells reach a minimum density. Subsequently, the propagated seed culture is transferred to a large-scale culture vessel containing culture medium lacking animal-derived components and propagated until at least a predetermined cell density is reached.

In this phase the cells are grown in suspension to allow the cell number within the culture vessel to increase to a predetermined or critical value. The medium exchange is performed by continuously perfusing the culture vessel with fresh medium.

The amount of perfused medium depends on the cell density and may typically be from 10-300%, preferably from 10% to 95%, 25% to 80%, of the tank volume per day (24 hours).

When the cell density reaches the value suitable for initiation of production phase, 60-95% of the tank medium in the tank is changed every 24 hours, preferably 80%. An 80% medium exchange is also preferably used in the production phase.

In the growth phase the culture is propagated until the cells reach a certain density. Reaching this density, the culture enters the production phase.

Setpoints may also be changed at this point and set at values suitable for production of the respective vitamin K-dependent protein. The medium perfusion is preferably performed continuously. The flow rate of medium can be expressed in terms of percentage tank volume of medium per defined period of time. Medium perfusion may be from 10-200% tank volume per 10-48 hours; preferably, the medium perfusion is 90% per 10-48 hours, more preferred 80% tank volume every 24 hours.

Cell retention within the culture vessel may be achieved using a number of cell retention devices. The following sets of apparatus may all be used for this process.

1. External settling head.
2. Internal settling head
3. Continuous centrifuge
4. Internal or external spin filter.
5. External filter or hollow fibre cartridge.
6. Ultrasonic cell separating device
7. A length of pipe inside the culture vessel.

2. Batch Processes:

2.1 Simple Batch Process:

In a simple batch process the cells are inoculated into a seed culture vessel containing culture medium lacking animal-derived components and propagated until the cells reach a minimum density. Subsequently, the propagated seed culture is transferred to a large-scale culture vessel containing culture medium preferably lacking animal derived components. The culture vessel is then operated until the nutrients in the medium are exhausted.

The time of harvest has to be determined. A traditional batch is operated until all nutrients become exhausted. However, this typically causes cell lysis, which either can be damaging to the product or may cause problems to purification.

2.2 Fed-Batch Process:

As stated previously a simple batch process consists inoculating a culture vessel with cells and operating the tank until the nutrients in the medium are exhausted. A batch process such as this can be extended by feeding a concentrated solution of nutrients to the tank. This extends the process time and ultimately leads to an increase in production of the respective vitamin K-dependent protein within the culture vessel.

Usually the most critical nutrient in the culture vessel is the glucose concentration. The control and initiation of the feed may thus be linked to the level of this nutrient. When the glucose concentration falls below a critical value a feed is initiated and the amount of feed added is sufficient to raise the glucose concentration back to this critical value.

Like in a simple batch process the time of harvest has to be determined as a balance between the longest possible operation of the tank and the risk of cell lysis and decrease in product quality.

The method of addition of the feed is also a variable. The feed can be added either as a single pulse (once, twice, three times etc., a day) or can be fed gradually throughout a 24-hour period. The time of harvest has to be determined. A traditional, or simple, batch is operated until all nutrients become exhausted. However, the process cannot be sustained indefinitely due to the accumulation of toxic metabolites. This leads to a decrease in cell viability and ultimately cell lysis. This may cause damage to the product or cause problems to subsequent purification.

3. Draw-Fill Processes:

A simple draw-fill process closely resembles a repeated batch fermentation. In batch fermentation the cells grow in the culture vessel and the medium is harvested at the end of the run. In a draw-fill process the culture vessel is harvested before any of the nutrients become exhausted. Instead of removing all of the contents from the vessel, only a proportion of the tank volume is removed (typically 80% of the tank volume).

After the harvest, the same volume of fresh medium is added back to the vessel. The cells are then allowed to grow in the vessel once more and another 80% harvest is taken a set number of days later. In repeated batch processes the cells left in the vessel after a harvest may be used as the inoculum for the next batch.

The process may be operated in two phases, with a first phase operated identically to a simple batch process. After the first harvest, the culture vessel is again operated as a simple batch process; however, the length of the batch is shorter than the first batch because of the higher initial cell density. These short 'repeated batch phases' can be continued indefinitely.

The culture vessel may be operated within a broad range of cycle times and a broad range of draw-fill volumes.

In practicing the present invention, the cells being cultivated are preferably mammalian cells, more preferably an established mammalian cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., J. Gen. Virol. 36: 59-72, 1977) cell lines.

A preferred CHO cell line is the CHO K1 cell line available from ATCC. Another preferred CHO cell line is the CHO-S cell line available Invitrogen.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, Proc. Natl. Acad. Sci. USA 77: 4216-4220, 1980) (DUKX cells also being referred to as DXB11 cells), and DG44 (CHO cell line) (Cell, 33: 405, 1983, and Somatic Cell and Molecular Genetics 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived.

In some embodiments, the cells used in practicing the invention are capable of growing in suspension cultures. As used herein, suspension-competent cells are those that can grow in suspension without making large, firm aggregates, i.e., cells that are monodisperse or grow in loose aggregates with only a few cells per aggregate. Suspension-competent cells include, without limitation, cells that grow in suspension without adaptation or manipulation (such-as, e.g., hematopoietic cells or lymphoid cells) and cells that have been made suspension-competent by gradual adaptation of attachment dependent cells (such as, e.g., epithelial or fibroblast cells) to suspension growth.

In some embodiments, the cells used in practicing the invention are adhesion cells (also known as anchorage-dependent or attachment-dependent cells). As used herein, adhesion cells are those that need to adhere or anchor themselves to a suitable surface for propagation and growth. Microcarrier based fermentation is an example for such an embodiment.

The present invention encompasses cultivating mammalian cells in media preferentially lacking animal-derived components. As used herein "animal-derived" components are any components that are produced in an intact animal (such as, e.g., proteins isolated and purified from serum) or are components produced by using components produced in an intact animal (such as, e.g., an amino acid made by using an enzyme isolated and purified from an animal to hydrolyse a plant source material). By contrast, a protein which has the sequence of an animal protein (i.e., has a genomic origin in an animal) but which is produced in vitro in cell culture (such as, e.g., in a recombinant yeast or bacterial cell or in an established continuous mammalian cell line, recombinant or not), in media lacking components that are produced in, and isolated and purified from an intact animal is not an "animal-derived" component (such as, e.g., insulin produced in a yeast or a bacterial cell, or insulin produced in an established mammal cell line, such as, e.g., CHO, BHK or HEK cells, or interferon produced in Namalwa cells). For example, a protein which has the sequence of an animal protein (i.e., has a genomic origin in an animal) but which is produced in a recombinant cell in media lacking animal derived components (such as, e.g., insulin produced in a yeast or bacterial cell) is not an "animal-derived" component. Accordingly, a cell culture medium lacking animal-derived components is one that may contain animal proteins that are recombinantly produced; such medium, however, does not contain, e.g., animal serum or proteins or other products purified from animal serum. Such medium may, for example, contain one or more components derived from plants.

Any cell culture medium lacking animal-derived components that supports cell growth and maintenance under the conditions of the invention may be used. Typically, the medium contains water, an osmolality regulator, a buffer, an energy source, amino acids, an inorganic or recombinant iron source, one or more synthetic or recombinant growth factors, vitamins, and cofactors. Media lacking animal-derived components and/or proteins are available from commercial suppliers, such as, for example, Sigma, SAFC, Invitrogen and Gibco.

The culture vessels may be e.g. conventional stirred tank reactors (CSTR) where agitation is obtained by means of conventional impeller types or airlift reactors where agitation is obtained by means of introducing air from the bottom of the vessel. Among the parameters controlled within specified limits are pH, dissolved oxygen tension (DOT), and temperature. The pH may be controlled by e.g. varying the C02 concentration in the headspace gas and/or sparger and by addition of base to the culture liquid when required.

Dissolved oxygen tension may be maintained by e.g. sparging with air or pure oxygen or mixtures thereof. The temperature-control medium is water, heated or cooled as necessary. The water may be passed through a jacket surrounding the vessel or through a piping coil immersed in the culture.

Once the medium has been removed from the culture vessel, it may be subjected to one or more processing steps to obtain the desired protein, including, without limitation affinity chromatography, hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J.-C. Janson and Lars Ryden, editors, VCH Publishers, New York, 1989.

The culture can be carried out in any suitable fermentation vessel, with a growth media and under conditions appropriate for the expression of the vitamin K-dependent protein(s) by the particular host cell chosen as described above. At some point during the expression phase of the desired vitamin K-dependent protein of interest a reduced form of vitamin K, and/or a reduced form of a vitamin K analog and/or a reduced form of a vitamin K precursor is comprised in the cell culture medium. Preferably said reduced form of vitamin K, and/or a reduced form of a vitamin K analog and/or a reduced form of a vitamin K precursor is present during the whole growth and the expression phase. In preferred embodiments, vitamin K-dependent protein can be collected directly from the culture media, or the host cells lysed and the vitamin K-dependent protein collected therefrom. In preferred embodiments, vitamin K-dependent protein can then be further purified in accordance with known techniques.

The recombinant vitamin K-dependent protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

As a general proposition, the purity of the recombinant protein produced according to the present invention will preferably be an appropriate purity known to the skilled art worker to lead to the optimal activity and stability of the protein. For example, when the recombinant protein is Factor IX, the Factor IX is preferably of ultrahigh purity.

Preferably, the recombinant protein has been subjected to multiple chromatographic purification steps, such as affinity chromatography, ion-exchange chromatography, hydrophobic interaction chromatography, dye chromatography, hydroxyapatite chromatography, size exclusion chromatography and preferably immunoaffinity chromatography to concentrate the desired protein and to remove substances which cause fragmentation, activation and/or degradation of the recombinant protein during manufacture, storage and/or use. Illustrative examples of such substances that are preferably removed by purification include other protein contaminants, such as modification enzymes like PACE/furin, VKOR, and VKGC; proteins, such as host cell proteins, which are released into the tissue culture media from the production cells during recombinant protein production; non-protein contaminants, such as lipids; and mixtures of protein and non-protein contaminants, such as lipoproteins. Purification procedures for vitamin K-dependent proteins are known in the art. For example, see U.S. Pat. No. 5,714,583, which is incorporated herein by reference.

In order to minimize the theoretical risk of virus contaminations, additional steps may be included in the process that allow effective inactivation or elimination of viruses. Such steps e.g. are heat treatment in the liquid or solid state, treatment with solvents and/or detergents, radiation in the visible or UV spectrum, gamma-radiation or nanofiltration.

Gene sequences for FIX and for other vitamin K dependent coagulation factors are known and available, for example, Factor II (Accession No. NM_000506), Factor VII (Accession No. NMJH9616, FIX ((Accession No. NM_000133) and Factor X (Accession No. NM_000504).

The vitamin K-dependent protein as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3rd edition, Kibbe et al., Pharmaceutical Press (2000)). In particular, the pharmaceutical composition comprising the protein variant of the invention may be formulated in lyophilized or stable liquid form. The protein variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially, the compositions of the invention are administered systemically. For systemic use, insertion proteins of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential routes of administration are intravenous and subcutaneous administration. The formulations can be administered continuously by infusion or by bolus injection. Some formulations encompass slow release systems.

The insertion proteins of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The pharmaceutical composition of the invention may be administered alone or in conjunction with other therapeutic agents. These agents may be incorporated as part of the same pharmaceutical.

EXAMPLES

Example 1

Cloning of the Factor IX Construct

Human coagulation Factor IX cDNA was cloned in-frame 5' to human albumin cDNA with the two cDNAs separated by a FIX-derived linker sequence. This linker sequence between FIX and albumin was derived from an endogenous FIX sequence involved in FIX activation, thus enabling the cleavage of the fusion protein by the same enzymes (FXIa or FVIIa/TF) which activate FIX.

The FIX sequence utilised threonine at position 148, the most prevalent phenotype at the site of a known Ala/Thr polymorphism and included a P-3V mutation to optimize propeptide cleavage (not present in the secreted product). The albumin signal peptide replaced that of FIX and the resulting cDNA sequence was codon-optimised for efficient mammalian cell expression. The protein coding sequence was flanked by a HindIII restriction site and a consensus Kozac sequence at the 5'end and an EcoRI restriction site at the 3' end. The nucleotide is SEQ ID NO:1 [signal sequence by 1-60, propeptide by 61-123), FIX (bp 124-1368), linker by 1369-1422), albumin (bp 1423-3180)] and the amino acid sequences of the resulting rIX-FP protein is SEQ ID NO:2 [FIX sequence (aa 1-415), linker sequence (aa 416-433); albumin sequence (aa 434-1018)].

The rIX-FP sequence was cloned into the Lonza GSTM expression vector pEE12.4 and a human PACE/Furin serine protease cDNA was cloned into the Lonza GSTM expression vector pEE6.4. PACE/Furin is required for efficient cleavage of the propeptide sequence in high expressing cell lines. Both rIX-FP and PACE/Furin cDNA's, under the control of individual CMV promoters, were combined to generate a final double gene construct.

Example 2

Transfection and Selection of Clones A2 and A5

The rIX-FP-PACE/Furin construct was electroporated into CHOK1SV cells and colonies were selected in 96 well plates using commercial glutamine free media. The resultant colonies were then screened for FIX expression and activity and two clones (A2 and A5) with the desired expression/activity profiles were chosen for further development.

Example 3

Manufacture of Reduced Menadione Bisulfite (rMSB)

The procedure involves in situ reduction of menadione sodium bisulphite (MSB) using an aqueous solution of ascorbic acid and catalytic addition of zinc powder. The resulting filtered reaction mixture contains MSB and the two corresponding isomeric reduction products (shown in FIG. 3 as No. 2 and No. 3, the reduced vitamin K), in the presence of ascorbic acid and traces of Zn. This filtrate mixture is used as the final product mixture.

Ascorbic acid (12.75 g) was dissolved in degassed Milli Q water (100 mL) in a 200 mL measuring cylinder with a fitted stopper.

Menadione sodium bisulphite (10.00 g) was dissolved in degassed Milli Q water (50 mL) in a 100 mL beaker and added to the ascorbic acid solution. The beaker was rinsed twice with 2×20 mL of degassed Milli Q water into the 200 mL measuring cylinder. The resulting ascorbic acid/menadione sodium bisulphite solution was made up to 200 mL with degassed Milli Q water and mixed by inverting the reaction vessel for 10 minutes at room temperature.

Activated zinc was prepared according to Textbook of Practical Organic Chemistry; Arthur Israel Vogel, A. R. Tatchell, B. S. Furnis. [year, editor]. Briefly, to 40 g of zinc powder in a 50 mL polypropylene tube, 15 mL of 10% v/v hydrochloric acid was added. The mixture was shaken and left to stand for 2 minutes. The mixture was transferred to a 500 mL Pyrex beaker and washed several times with Milli Q water. This also involved copious elutriation with Milli Q water to remove fines. The rinsed activated zinc was suspended in Milli Q water and transferred to a filter apparatus where it was trapped on a 0.45 μm Durapore® GV membrane. The zinc was washed several times with 50 mL HPLC grade Acetonitrile prior to drying on a rotary evaporator at 60° C. for 1.5 hours. The dried activated zinc was stored in a Pyrex bottle under Argon.

Activated zinc powder (4.73 g) was added to the ascorbic acid/menadione sodium bisulphite solution and mixed by continuous gentle inversion of the measuring cylinder for 25-30 minutes.

Upon completion the solution was filtered under vacuum through a 0.22 μm Durapore® GV membrane. The filtrate was then transferred to a sterile bottle, flushed with Argon, covered with foil to protect from light and stored at −70 C. This filtrate was added to the bioreactors.

Reduced MSB is expected to be, to a certain extent, unstable. Therefore the actual concentration of rMSB when added to the bioreactor might be somewhat lower than the stated concentration (see analytical data below). Therefore, as used in the present invention, a stated concentration of rMSB should be understood as a nominal concentration corresponding to the actual MSB concentration used to generate rMSB as detailed in Example 3 Assay of reduced MSB Reduced MSB was assayed by reversed phase HPLC coupled with electrospray ionization mass spectrometry (ESI-MS).

The HPLC separation was achieved using a Merck Supersher RP-Select B (4.0×75 mm) column with 10 mM ammonium acetate buffer as Buffer A and 95% Acetonitrile, 10 mM ammonium acetate as Buffer B.

The following gradient was used.

| Time (mins) | % Buffer A | % Buffer B |
|---|---|---|
| 0.0 | 95 | 5 |
| 8.0 | 85 | 15 |
| 8.1 | 95 | 5 |
| 15.0 | 95 | 5 |

Menadione sodium bisulphite (Sigma Lot 087K0737, 97% by C of A) was used to prepare standards.

The Waters Q-ToF II mass spectrometer was operated in negative ion mode and extracted ion chromatograms at m/z of 253 for menadione bisulphite were integrated and used to plot a five point calibration curve fitted to a second order polynomial (not forced through zero).

Extracted ion chromatograms of reduced menadione bisulphite at m/z 255 of were bisulphite were integrated and used to calculate the concentration of reduced menadione bisulphite against the calibration curve obtained with the MSB standard.

Results are summarized in the following table (50 mg/mL nominal concentration of rMSB).

| Batch Number | Red MSB (mg/mL) |
|---|---|
| CSL 080508 | 47.7 |
| CSL 211008 | 47.9 |
| Epichem 1 | 49.9 |

Example 4

A CHO cell line expressing recombinant Factor IX fusion protein with human albumin was generated as detailed in Examples 1 and 2. To investigate a method of increasing the expression of the active molecule a number of experiments were performed assessing the effect of the addition of menadione sodium bi-sulphite (MSB) and reduced MSB (rMSB) to the cultures. The aim of this investigation was to identify if either of the MSB or rMSB additions were able to either increase the expression of active molecule or to decrease the amount of antigenic material expressed. The activity of the molecule was assessed by a specific factor IX assay kit, with the assumption that an increase in activity will be due to an increase in gamma-carboxylation of the glutamic acid residues on the molecule, driven by the availability of Vitamin K3.

The medium used in all instances for propagation of the cells and during productivity assessments was a chemically defined medium, designated here as Medium A as detailed below. In instances where other media types were used for comparison purposes they are described in the text. The key parameters measured during this investigation were the antigenic expression of recombinant factor IX fused with human Albumin (rIX-FP), the FIX activity resulting from this expression and the cell growth as measured by viable cell density. The specifics of measuring these key cellular outputs are described below.

Methods and Materials:

Medium Composition

The medium used for the propagation was a commercially obtainable serum-free chemically defined medium specifically designed for the production of recombinant proteins in CHO cells: "Medium A". The clones utilised the Lonza glutamine synthetase (GS) system and were passaged in the absence of glutamine with selection maintained by 25 uM methionine sulfoximine (MSX). In the last culture stage, used for productivity measurement, both glutamine and MSX were not added to the medium.

Bolus Additions

Bolus additions of 100 g/L glucose were made to the culture when glucose concentrations reached a lower limit of 2 g/l, once the lower limit concentration was met, a feed was instigated to increase the residual medium concentration to an upper amount of 4 g/l.

Vitamin K is essential to the cell for the production of active recombinant Factor IX, due to the Vitamin K-dependent gamma-carboxylation of the molecule. In experiments describing the present invention Vitamin K3 in the form of Menadione sodium bi-sulphate (MSB, Sigma) was chosen as the source of Vitamin K as this form is water soluble and thus readily accessible to the cell. Addition of MSB occurred daily at a concentration of 50 ng/ml.

Reduced MSB (rMSB) was prepared as previously described in example 3. The rMSB was stored at −70° C. and thawed immediately prior to use. Due to the inherent unstable nature of the reduced MSB, quantification of exact concentrations of the reduced MSB was not available at the time of experimentation. Therefore all stated concentrations of reduced MSB are calculated values derived from the starting concentration of MSB at the commencement of the reduction process. It is anticipated that the actual reduced MSB concentration is less than the calculated amount due to some small losses occurring through the reduction process.

Fermentation Parameters.

The reactors were Sartorius/Braun 5 L dished bottom glass reactors, with a single Rushton Impeller for agitation and a ring sparger. All reactor cultures were performed under the following conditions unless otherwise stated.

Volume: Starting at 4 liters total (3.2 liters media and 0.8 liter inoculum);

Temperature: 37° C., from inoculation until harvest;

Aeration: Headspace air at 0.0375 void volumes per minute vvm for the duration, sparged in response to dissolved oxygen (D.O.) set-point at a maximal rate of 0.025 vvm;

D.O.: Set-point of 40% saturation;

Oxygen: Sparged in response to D.O. set-point at maximal flow-rate of 0.075 vvm;

Agitation: At a constant rate of 100 rpm;

pH: Single set-point of 7.00±0.05;

Base: 2M NaOH;

Acid: 100% CO2;

Inoculum: Starting cell density of $3\times10^5$-$5\times10^5$ cells/mL.

Cell Culture Assays:

Cell counts were performed utilising the Innovartis Cedex automated cell counter in accordance with the manufacturers instructions. Glucose, lactate, ammonia and glutamine assays were performed utilising the Yellow Springs Instruments (YSI) 7100 analyser in accordance with the manufacturers instructions. Off-line determination of dissolved carbon dioxide concentrations were performed using the RapidLab 248 Blood Gas Analyser from Siemens (formerly Bayer) in accordance with the manufacturer's instructions. Antigen assay was performed using an internal procedure ELISA for Quantitation of Factor IX Antigen. The Factor IX Activity assay was performed using the "BIOPHEN FIX" chromogenic FIX test. Sampling was performed daily from the point of inoculation for all assays.

Flask Productivity Assay

The Flask productivity assay was performed as described below.

A CHO-S cell line expressing rIX-FP was used and cultured in an alternative commercially obtainable serum-free chemically defined medium specifically designed for the production of recombinant proteins in CHO cells ("Medium B") with 8 mM L-glutamine. In the N−1 and N (with N being the last passage number) passage 50 ng/ml MSB was added. Another addition was performed at 48 hours post inoculation. Cultures were inoculated at $2\times10^5$ viable cells/mL at a 30 mL volume in a 125 mL shake flask, cultured at 37 C, 5% $CO_2$, 125 rpm in a humidified incubator (Multitron, Infors HT). Samples were assayed for cell density, cell viability, rIX-FP activity and antigen content.

Results:

Experiment 1: Comparison of FIX Expression in Shake Flasks

Experiment 1 was performed to assess the effect of reduced MSB on culture performance compared to additions of MSB in a flask format. A summary of the test conditions investigated in this experiment are presented in Table 1. The cells were subjected to the standard flask productivity assay with assays for cell density, Factor IX antigen and Factor IX activity performed. A summary of the results obtained from this Flask productivity assay are presented in Table 2 and Table 3.

TABLE 1

The flask test conditions used in Experiment 1

| Reduced or Non Reduced MSB | Number of additions | Flask Number |
|---|---|---|
| Non-Reduced | 1 | C1.0 |
| Non-Reduced | 1 | C1.1 |
| Non-Reduced | 2 | C2.0 |
| Non-Reduced | 2 | C2.1 |
| Reduced | 1 | D1.0 |
| Reduced | 1 | D1.1 |
| Reduced | 2 | D2.0 |
| Reduced | 2 | D2.1 |

The activity results for 72 hour and 96 hr are presented below. They show very similar results obtained at 72 hr for all test conditions. There is a slight increase in activity obtained for the two additions of MSB, and all results using the reduced MSB are slightly higher than non-reduced MSB additions. Interestingly there is no increase for two additions for the reduced MSB condition. The interpretation of the results at 72 hours is limited however due to the small number of replicates and the small differences in activity results between the conditions.

A more definite increase in activity result was obtained for the 96 hr sample. In this instance the reduced MSB condition returned greater activity results than that obtained for the MSB addition. All recorded values are means of duplicate flasks.

TABLE 2

Flask Productivity experimental results for 72 hours

| Experimental Condition | Flasks | Activity | Antigen | Ratio |
|---|---|---|---|---|
| MSB single addition | C1.0, C1.1 | 357.5 | 625.5 | 0.57 |
| MSB double addition | C2.0, C2.1 | 431.5 | 451.5 | 0.96 |
| Reduced MSB single addition | D1.0, D1.1 | 500 | 516 | 0.97 |
| Reduced MSB double addition | D2.0, D2.1 | 477 | 514.5 | 0.93 |

TABLE 3

Flask Productivity experimental results for 96 hours

| Experimental Condition | Flask | Activity | Antigen | Ratio |
|---|---|---|---|---|
| MSB single addition | C1.0, C1.1 | 629.5 | 2573 | 0.24 |
| MSB double addition | C2.0, C2.1 | 649 | 1155.5 | 0.56 |
| Reduced MSB single addition | D1.0, D1.1 | 1070.5 | 1249 | 0.86 |
| Reduced MSB double addition | D2.0, D2.1 | 902 | 1271 | 0.71 |

From the results presented in Table 2 and 3 a positive effect on the production of active FIX and an increase in the active FIX molecule in proportion to FIX antigen (Ratio) was observed with the addition of reduced MSB compared to the addition of MSB.

The preliminary results obtained from the flask productivity work indicated that there may be differences in active molecule secretion by the cell due to the presence of a reduced form of MSB being present. To test the effects of reduced MSB on the production of rIX-FP in CHO cells, reactor based experiments were performed.

Experiment 2: Comparison of FIX Expression Under Fed-Batch Conditions

Under reactor fed-batch conditions a rIX-FP CHO-K1 clone was cultivated under the standard conditions. This experiment assessed the cell growth, antigen production and active rIX-FP production from the cell under either MSB addition or reduced MSB addition. The feed utilised in this experiment was glucose based (100 g/l) supplemented with the following amino acids:
- Asparagine at 21.4 g/L;
- Cysteine at 5.6 g/L;
- Aspartic acid at 5 g/L.

The reactor test conditions were Reactor A4 utilising a non-reduced MSB addition and Reactor B4 utilising a reduced MSB addition. In both reactors Medium A was used as described in Example 4.

The cell growth results obtained from the culture are shown in FIG. 4.

The above data shows that the viable cell densities for the two conditions (reduced and non-reduced MSB) obtained very similar growth profiles and maximum cell densities. Under these two conditions, the only difference was the intended comparison between reduced and non reduced MSB. The assay results for antigen, active molecule and the respective ratio is presented in Table 4. A ratio above one of active molecule to antigen is possible as the IU they are each measured against have different standard references to plasma.

TABLE 4

Comparison of the total active and antigen produced under Reactor A4 MSB, and Reactor B4 reduced MSB (data obtained for both reactors up to 192 hour post inoculation).

| Parameter | Reactor A4 MSB | Reactor B4 rMSB |
|---|---|---|
| Approximate Volume (L) | 4 | 4 |
| Activity (U) | 22357 | 35444 |
| Antigen (U) | 49479 | 38197 |
| Ratio | 0.45 | 0.93 |

The higher ratio produced in this instance under the reduced MSB addition conditions was caused by an increase in the active FIX molecule produced, and a decrease in the FIX antigen level produced compared to the MSB addition condition.

Experiment 3: Comparison of FIX Expression Under Extended Draw-Fill Conditions

The CHO-K1 clone A5 was cultivated under extended draw-fill conditions with two media, Media A and yet another commercially obtainable serum-free chemically defined medium specifically designed for the production of recombinant proteins in CHO cells: Media C. While comparing the performance of the media, the effect of the addition of MSB or reduced MSB was assessed (Table 5). As with previous experiments the outputs from this investigation were growth parameters of the cell and the production of active rIX-FP molecule and rFIX-FP antigen.

TABLE 5

Reactor test conditions used in Experiment 3

| Reactor | Media | Vitamin K |
|---|---|---|
| A2 | Medium A | Reduced |
| A4 | Medium A | Non-reduced |
| B2 | Medium C | Reduced |
| B4 | Medium C | Non-reduced |

In this investigation a difference in terms of cell growth was observed. This difference was that greater cell numbers were able to be achieved in Medium A. There was very little difference in relation to cell growth between the reactors comparing reduced and non-reduced MSB at this concentration of MSB/rMSB (50 ng/ml per day).

The FIX antigen and the active FIX molecule production of the cells under the different test conditions were analysed. A summary of these results is presented in Table.6 There are substantial differences evident under the extended draw-fill combination. Medium A produced 20%-30% higher antigen and 22%-27% higher activity than Medium C from similar culture volumes.

TABLE 6

Comparison of the antigenic and activity assay results for Experiment 3.

| Parameter | Reactor A2 rMSB | Reactor A4 MSB | Reactor B2 rMSB | Reactor B4 MSB |
|---|---|---|---|---|
| Approximate Volume (L) | 7 | 7 | 7 | 7 |
| Activity (U) | 30580 | 28864 | 24052 | 23570 |
| Antigen (U) | 46254 | 58987 | 38528 | 45443 |
| Ratio | 0.66 | 0.49 | 0.62 | 0.52 |

Experiment 4: Effect of MSB and rMSB on Cell Growth and Viability

To test the effect of increasing concentrations of MSB and reduced MSB on cell growth and viability, a further investigation was undertaken. Eight reactors were cultivated under identical parameters, with the exception of either MSB addition or reduced MSB addition. As with the previous experiments the concentration of reduced MSB was a calculated value, and the true concentration may be lower than the calculated value. The medium used was Medium A as described in Experiment 1. The additions were increased on a per cell basis each day (Table 7), and the effect on cell growth were monitored. The reactors were performed in draw-fill mode with the first cycle having a duration of 6 days, and the second cycle a duration of 4 days.

TABLE 7

Reactor test conditions used in Experiment 4

| Reactor | [MSB] | Vitamin K |
|---------|-------|-----------|
| A1 | 50 ng/mL = 200 µg/day | Non-reduced |
| A2 | 240 µg/109 cells/day | Non-reduced |
| A3 | 720 µg/109 cells/day | Non-reduced |
| A4 | 2160 µg/109 cells/day | Non-reduced |
| B2 | Nominal 240 µg/109 cells/day | Reduced |
| B3 | Nominal 720 µg/109 cells/day | Reduced |
| B4 | Nominal 2160 µg/109 cells/day | Reduced |

The viable cell density and cell viability data is presented in FIGS. 6 and 7 respectively.

Reactors A3 and A4 were terminated before the completion of the experiment, and this is reflected in the data plots. The reactors were terminated early as the increasing MSB concentration was causing cell death within the reactor. The observed cell death in the reactor was reflected in a decreased demand for oxygen. Reactor A4 contained the highest MSB concentration and began its decline first, followed by Reactor A3 with the second highest MSB concentration. Cell death of reactor A4 commenced within 10 hours of the commencement of cell death in reactor A3.

Experiment 5: Cell Viability Data Under Increasing Titration of MSB and Reduced MSB.

This work was undertaken to assess the performance of MSB and reduced MSB additions on the cell growth and productivity of the active Factor IX Fusion protein molecule. Initially flask experiments were performed with a CHO-S clone to gain data to support further investigation. In this experiment, data was collected at both the 72 hour and 96 hour time points. At 72 hours increased activity yield was achieved with the reduced MSB additions. Antigenic yield also increased compared to the MSB additions; however the highest ratio was maintained by the reduced MSB additions. In this instance a single addition of reduced MSB gave increased but comparable activity yields than a double addition of MSB. The data collected at the 96 hour time point showed only slight increases in activity for the reduced MSB additions. However all reduced MSB addition flasks maintained an equivalent or higher ratio compared to the MSB additions. Overall, increased ratio and equivalent or increased activity expression was obtained from the addition of reduced MSB compared to MSB addition.

When expressing an inherently unstable protein, culture formats such as perfusion or draw-fill are desirable as it allows removal of the spent medium and subsequent purification and stabilisation of the desired protein. To further extend the cells capability and to illuminate the possible effects of the addition of reduced MSB compared to MSB additions, a fed-batch culture was performed. The results of this investigation were presented in Experiment Two. Under fed-batch conditions similar growth was achieved under either reduced MSB or MSB additions (Refer FIG. 4). The data shows that under reduced MSB addition conditions the amount of active rIX-FP was increased from 22357 IU to 35444 IU, representing a 59% increase. Interestingly concurrent with the observed increase in active molecule, was a decrease in the antigenic yield to 38197 IU, representing 77% of the MSB value. The increase in active and decrease in antigenic material resulted in a large increase in ratio due to the addition of reduced MSB.

To test the cells response in draw-fill mode, a CHO-K1 clone was cultured in two media, and again the effect of MSB and reduced MSB addition was evaluated. The growth of the cells did differ relative to the test medium (Refer FIG. 5). Growth to higher cell densities was obtained with Medium A. The duplicates within each medium test however were very reproducible, again showing that there was little or no difference in growth characteristics due to the addition of MSB or reduced MSB at the concentrations tested. As with previous experiments the amount of active molecule and antigenic molecule was assayed. For both media types higher activity values were obtained with the reduced MSB addition, though in this instance the increase was very small with the MSB addition values in the range of 94-98% of the reduced MSB addition values. The greater difference was observed in the amount of antigenic material produced under the test conditions. For both media A and C the reduced MSB addition reactors produced less antigenic material than that from the MSB additions. When cultured in Medium A, reduced MSB produced 78% of antigenic material, and in Medium C produced 84% of antigenic material compared to MSB additions. This resulted in an increase in ratio of 19-35% depending on media type, delivered by the reduced MSB additions.

The final experiment was designed to test the levels of MSB and reduced MSB that would be tolerable to the cell. The output from this investigation were the cell viability and viable cell density achieved during these cultures (refer Figure Six and Figure Seven respectively). The control condition used was 50 ng/ml MSB added daily, and cell numbers and viability achieved under these conditions were as expected and in line with previous results. With the increase of MSB addition to 210 ug/10^6 cells/day a substantial decrease in cell viability and cell number were observed. The further decreases in cell viability and cell number observed at both 720 and 2160 ug/10^6 cells/day indicate that the MSB additions were increasingly toxic to the cell at increasing concentrations.

The toxicity effect of additions were also observed with the reduced MSB, though be it to a lesser extent. The concentrations used for the reduced MSB additions were nominal calculated values as stated previously. Cell growth was comparable to the control for both the 240 and 720 ug/10^6 cells/day additions. The toxicity observed did not result in cell death, but in reduced cell growth for the 2160 ug/10^6 cells/day reduced MSB addition, in stark contrast to the equivalent MSB condition. These results indicate that at the concentrations used reduced MSB had a much less toxic effect on the cells than addition of MSB.

The effect of MSB and reduced MSB additions has been evaluated in a range of culture formats. A consistent result achieved from these investigations under comparable conditions was that reduced MSB addition returned either equivalent or increased activity yields and decreased antigenic yields compared to MSB addition. The toxicity of the reduced MSB appears to be less, as demonstrated by tolerance by the cell at higher concentrations; The exact mechanism of action of the reduced MSB effect has not been fully elucidated. The effect could be through enhanced entry into the cell, increased stability of the reduced MSB in culture, or within the cell cytoplasm, or a direct mechanism on the gamma carboxylation pathway of the cell. Though the exact mechanism is not clear, the end result of addition of reduced MSB to the cultures is of increased ratio of expressed active material in relation to total antigenic material. In the context of production of recombinant rIX-FP this represents a significant advantage.

Experiment 6:

An albumin fused Factor VII was cloned and expressed in CHO-S cells as described in Thromb. Haemost. 2008 April; 99(4):659-67.

Cultivation of mammalian cells occurred under either batch or fed-batch conditions at a starting volume of 3 liters in a 5 liter bioreactor system. Controlled parameters were temperature (37° C.), pH (7.2), agitation (250 rpm) and dissolved oxygen. The medium used was a commercially available, chemically defined media (CD-CHO, Invitrogen) which was supplemented with MSB or rMSP in a starting concentration of 50 ng/ml. Each day the concentration was increased by 50 ng/ml until on day 5 a maximum concentration of 250 ng/ml was reached, which was then held for the remainder of the cultivation period. The duration of cultivation did not exceed 12 days.

The activity of FVII was determined using a chromogenic assay (COASET® FVII test kit (Chromogenix, 82190063)). The amount of protein was determined via reverse phase HPLC.

| Effect on Specific Activity (IU/mg) | | | |
| --- | --- | --- | --- |
| Vitamin K Presentation | Mean | Lower 95% Confidence Interval | Upper 95% Confidence Interval |
| Menadione Sodium Bisulphite (MSB; n = 4) | 313.5 | 266.3 | 360.7 |
| Reduced Menadione Sodium Bisulphite (rMSB; n = 25) | 392.6 | 373.7 | 411.5 |

The switch to rMSB from MSB has had the benefit of increasing the amount of active product expressed, both in the case of Factor IX and Factor VII. In each instance there has also been a corresponding increase in specific activity observed (See, e.g., FIG. 8(a) and FIG. 8(b)).

The invention claimed is:

1. A process for fermentation of mammalian cells, where the mammalian cells express one or more vitamin K-dependent proteins, the process comprising
fermenting the mammalian cells in a cell culture medium, and
adding one or more compounds to the cell culture medium before and/or during the fermenting, wherein at least one of the one or more compounds is selected from the group consisting of i) reduced forms of vitamin K, ii) reduced forms of vitamin K analogs, and iii) reduced forms of vitamin K precursors;
wherein
the vitamin K analog comprises a 2-methyl-1,4-naphthoquinone ring structure and can functionally substitute for vitamin K1 in the vitamin-K cycle dependent gamma carboxylation of glutamic acid residues to Gla-residues in vitamin K-dependent proteins and
the vitamin K precursor is a molecule that can be transformed by a mammalian cell to a compound that comprises a methylated naphthoquinone ring structure and can functionally substitute for vitamin K1 in the vitamin-K cycle dependent gamma carboxylation of glutamic acid residues to Gla-residues in vitamin K-dependent proteins.

2. The process according to claim 1, wherein the one or more vitamin K-dependent proteins comprises one or more vitamin K-dependent coagulation factors.

3. The process according to claim 1, wherein at least one of the one or more vitamin K-dependent proteins is selected from the group consisting of Factor IX (FIX), Factor VII (FVII), Factor X (FX), Factor II (FII), Protein C, Protein S, Protein Z, osteocalcin, calcification inhibiting matrix Gla protein (MGP), and cell growth regulating growth arrest specific gene 6 protein (Gas6).

4. The process according to claim 1, wherein at least one of the one or more vitamin K-dependent proteins is selected from the group consisting of FIX and FVII.

5. The process according to claim 1, wherein the one or more compounds is (a) reduced menadione bi-sulphite or (b) the reduced form of vitamin K precursor where the vitamin K precursor is selected from menadione, menadiol diphosphate, menadiol dibutyrate, menadiol disulphate, menadione nicotinamide bisulfite, and menadoxime.

6. The process according to claim 1, wherein the fermentation is performed in a bioreactor.

7. The process according to claim 1, wherein the fermentation is operated in a draw-fill mode.

8. The process according to claim 1, wherein the fermentation is operated in a batch mode.

9. The process according to claim 1, wherein the fermentation is operated in a perfusion mode.

10. The process according to claim 1, wherein the fermentation is performed using cells in suspension.

11. The process according to claim 1, wherein the fermentation is performed with adherent cells.

12. A composition for fermentation of vitamin K-dependent proteins comprising a cell culture medium and one or more extracellular compounds selected form the group consisting of reduced forms of vitamin K, reduced forms of vitamin K analogs, and reduced forms of vitamin K precursors;
wherein
the vitamin K analog comprises a 2-methyl-1,4-naphthoquinone ring structure and can functionally substitute for vitamin K1 in the vitamin-K cycle dependent gamma carboxylation of glutamic acid residues to Gla-residues in vitamin K-dependent proteins and
the vitamin K precursor is a molecule that can be transformed by a mammalian cell to a compound that comprises a methylated naphthoquinone ring structure and can functionally substitute for vitamin K1 in the vitamin-K cycle dependent gamma carboxylation of glutamic acid residues to Gla-residues in vitamin K-dependent proteins.

13. A composition comprising
(a) a transfected mammalian cell which expresses one or more vitamin K-dependent proteins, and
(b) one or more extracellular compounds selected form the group consisting of reduced forms of vitamin K, reduced forms of vitamin K analogs, and reduced forms of vitamin K precursors;

wherein
- the vitamin K analog comprises a 2-methyl-1,4-naphthoquinone ring structure and can functionally substitute for vitamin K1 in the vitamin-K cycle dependent gamma carboxylation of glutamic acid residues to Gla-residues in vitamin K-dependent proteins and
- the vitamin K precursor is a molecule that can be transformed by a mammalian cell to a compound that comprises a methylated naphthoquinone ring structure and can functionally substitute for vitamin K1 in the vitamin-K cycle dependent gamma carboxylation of glutamic acid residues to Gla-residues in vitamin K-dependent proteins.

14. The composition according to claim 13, wherein the one or more compounds is reduced menadione bi-sulphite.

15. The composition according to claim 13, wherein the one or more compounds is (a) reduced menadione bi-sulphite or (b) the reduced form of vitamin K precursor where the vitamin K precursor is selected from menadione, menadiol diphosphate, menadiol dibutyrate, menadiol disulphate, menadione nicotinamide bisulfite, and menadoxime.

16. The composition according to claim 13, wherein the reduced form of vitamin K, the reduced form of vitamin K analog, or the reduced form of vitamin K precursor is a hydroquinone form of a vitamin K, a hydroquinone form of a vitamin K analog, or a hydroquinone form of a vitamin K precursor, respectively, and the reduced form of vitamin K, the reduced form of vitamin K analog, or the reduced form of vitamin K precursor is accepted by the transfected mammalian cell without the need for a further reductive step as a co-substrate of vitamin K-dependent carboxylase in the carboxylation reaction transforming glutamic acid residues to Gla-residues in vitamin K-dependent proteins.

17. The process according to claim 1, wherein the reduced form of vitamin K, the reduced form of vitamin K analog, or the reduced form of vitamin K precursor is a hydroquinone form of a vitamin K, a hydroquinone form of a vitamin K analog, or a hydroquinone form of a vitamin K precursor, respectively, and the reduced form of vitamin K, the reduced form of vitamin K analog, or the reduced form of vitamin K precursor is accepted by the mammalian cells without the need for a further reductive step as a co-substrate of vitamin K-dependent carboxylase in the carboxylation reaction transforming glutamic acid residues to Gla-residues in vitamin K-dependent proteins.

* * * * *

SEQUENCE LISTING

```
<160> NUMBER OF SEQ ID NOS: 2

<210> SEQ ID NO 1
<211> LENGTH: 3180
<212> TYPE: DNA
<213> ORGANISM: Artificial Sequence
<220> FEATURE:
<223> OTHER INFORMATION: Fusion protein

<400> SEQUENCE: 1
atgaagtggg tgaccttcat cagcctgctg tttctgttca gcagcgccta cagcagaggc        60
gccgagtgta ccgtgttcct ggaccacgag aacgccaaca agatcctgaa cagggtgaag       120
aggtacaaca gcggcaagct ggaagaattt gtgcagggca acctggaacg ggagtgcatg       180
gaagaaaagt gcagcttcga ggaagccaga gaggtgttcg agaacaccga gaggaccacc       240
gagttctgga agcagtacgt ggacggcgac cagtgcgaga gcaaccctg cctgaacggc       300 ggcagctgca aggacgacat caacagctac gagtgctggt gccccttcgg cttcgagggc       360
aagaactgcg agctggacgt gacctgcaac atcaagaacg gcagatgcga gcagttctgc       420
aagaacagcg ccgacaacaa ggtggtgtgc tcctgcaccg agggctacag gctggccgag       480
aaccagaaga gctgcgagcc cgccgtgccc ttcccttgcg gaagggtgtc cgtgagccag       540
accagcaagc tgaccagggc cgagacagtg ttccccgacg tggactacgt gaacagcacc       600
gaggccgaga caatcctgga caacatcacc cagagcaccc agtccttcaa cgacttcacc       660
agggtggtgg gcggcgagga cgccaagccc ggccagttcc catggcaggt ggtgctgaac       720
ggcaaggtgg acgccttctg cggcggcagc atcgtgaacg agaagtggat cgtgacagcc       780
gcccactgcg tggagacagg cgtgaagatc accgtggtgg ccggggagca acatcgag       840 gaaacagagc acaccgagca aagaggaac gtcatcagga tcatccccca ccacaactac       900
aacgccgcca tcaacaagta caaccacgac atcgccctgc tggaactgga cgagccactg       960
gtgctgaaca gctacgtgac ccccatctgt atcgccgaca aggaatacac caacatcttt      1020
ctgaagttcg gcagcggcta cgtgagcggc tggggcaggt gttccacaa gggcaggtcc      1080 gctctggtgc tgcagtacct gagggtgccc ctggtggaca gggccacctg cctgaggtcc      1140
accaagttca catcatacaa caacatgttc tgcgccggct tccacgaggg cggcagggac      1200
agctgccagg gcgacagcgg cggacctcac gtgacagaag tggaggggac cagcttcctg      1260
```

```
accggcatca tcagctgggg cgaggaatgc gccatgaagg gcaagtacgg catctacacc    1320
aaggtgtcca gatacgtgaa ctggatcaaa gaaaagacca agctgacccc cgtgtcccag    1380
acctccaagc tgacacgcgc cgagacagtg tttccagacg tggacgccca agagcgag     1440 gtggcccaca ggttcaagga cctgggcgag gaaaacttca aggccctggt cctgatcgcc    1500
ttcgcccagt acctgcagca gtgcccattc gaggaccacg tgaagctggt gaacgaggtg    1560
accgagttcg ccaagacctg cgtggccgac gagagcgccg agaactgcga caagagcctg    1620
cacaccctgt tcggcgacaa gctgtgcacc gtggccaccc tgcgggagac atacggcgag    1680
atggccgact gctgcgccaa gcaggaaccc gagaggaacg agtgcttcct gcagcacaag    1740
gacgacaacc ccaacctgcc caggctggtg cggcccgagg tggacgtgat gtgcaccgcc    1800
ttccacgaca cgaggaaac attcctgaag aagtacctgt acgagatcgc cagaaggcac     1860
ccctacttct acgcccccga gctgctgttc ttcgccaaga gatacaaggc cgccttcacc    1920
gagtgctgcc aggccgctga caaagctgcc tgcctgctgc caaaactgga cgagctgagg    1980
gacgagggca aggcctcttc cgctaaacag aggctgaagt gcgccagcct gcagaagttc    2040
ggcgagaggg cctttaaggc ctgggccgtg gccaggctgt cccagaggtt ccccaaggcc    2100
gagtttgccg aggtgtccaa gctggtgacc gatctgacaa aggtgcacac cgagtgttgt    2160
cacggcgacc tgctggaatg cgccgacgac agagccgacc tggccaagta catctgcgag    2220
aaccaggaca gcatctcctc taagctgaag gaatgctgcg agaagccact gctggaaaag    2280
agccactgta tcgccgaggt ggagaacgac gagatgcccg ccgacctgcc ttctctggcc    2340
gccgacttcg tggagtccaa ggacgtgtgc aagaactacg ccgaggctaa ggatgtgttc    2400
ctgggcatgt tcctgtacga gtacgcccgc agacaccccg actacagcgt ggtgctgctg    2460
ctgaggctgg ccaagaccta cgagacaaca ctggaaaagt gctgcgccgc cgccgacccc    2520
cacgagtgct acgccaaggt gttcgacgag ttcaagcctc tggtggagga accccagaac    2580
ctgatcaagc agaactgtga gctgttcgag cagctgggcg agtacaagtt ccagaacgcc    2640
ctgctggtgc ggtacaccaa gaaggtgccc caggtctcca caccaaccct ggtggaggtg    2700
tccaggaacc tgggcaaagt cggaagcaag tgctgcaagc acccagaggc caagaggatg    2760
ccctgcgccg aggactacct gtccgtcgtc ctgaaccagc tgtgcgtgct gcacgaaaag    2820
acccccgtga cgacagggt gaccaagtgc tgtaccgaga cctggtgaa cagaaggccc      2880 tgcttcagcg ccctggaagt ggacgagaca tacgtgccca agagttcaa cgccgagaca     2940 ttcaccttcc acgccgacat ctgcaccctg agcgagaagg aaaggcagat caagaagcag    3000
accgccctgg tcgagctggt gaagcacaag cccaaggcca ccaaggaaca gctgaaggcc    3060
gtcatggacg acttcgccgc ctttgtggag aaatgttgta aggctgatga caaggaaaca    3120
tgcttcgccg aggaaggaaa gaaactggtc gccgcctctc aggctgctct gggcctgtga    3180
```

<210> SEQ ID NO 2
<211> LENGTH: 1018
<212> TYPE: PRT
<213> ORGANISM: Artificial Sequence
<220> FEATURE:
<223> OTHER INFORMATION: Fusion protein

<400> SEQUENCE: 2

```
Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30
```

```
Glu Asn Thr Glu Arg Thr Thr Glu Phe Trp Lys Gln Tyr Val Asp Gly
         35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
            115                 120                 125

Pro Phe Pro Cys Gly Arg Val Ser Val Ser Gln Thr Ser Lys Leu Thr
        130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
        210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
        290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
        370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr Pro
                405                 410                 415

Val Ser Gln Thr Ser Lys Leu Thr Arg Ala Glu Thr Val Phe Pro Asp
            420                 425                 430

Val Asp Ala His Lys Ser Glu Val Ala His Arg Phe Lys Asp Leu Gly
        435                 440                 445
```

```
Glu Glu Asn Phe Lys Ala Leu Val Leu Ile Ala Phe Ala Gln Tyr Leu
450                 455                 460
Gln Gln Cys Pro Phe Glu Asp His Val Lys Leu Val Asn Glu Val Thr
465                 470                 475                 480
Glu Phe Ala Lys Thr Cys Val Ala Asp Glu Ser Ala Glu Asn Cys Asp
                485                 490                 495
Lys Ser Leu His Thr Leu Phe Gly Asp Lys Leu Cys Thr Val Ala Thr
            500                 505                 510
Leu Arg Glu Thr Tyr Gly Glu Met Ala Asp Cys Cys Ala Lys Gln Glu
        515                 520                 525
Pro Glu Arg Asn Glu Cys Phe Leu Gln His Lys Asp Asp Asn Pro Asn
530                 535                 540
Leu Pro Arg Leu Val Arg Pro Glu Val Asp Val Met Cys Thr Ala Phe
545                 550                 555                 560
His Asp Asn Glu Glu Thr Phe Leu Lys Lys Tyr Leu Tyr Glu Ile Ala
                565                 570                 575
Arg Arg His Pro Tyr Phe Tyr Ala Pro Glu Leu Leu Phe Phe Ala Lys
            580                 585                 590
Arg Tyr Lys Ala Ala Phe Thr Glu Cys Cys Gln Ala Ala Asp Lys Ala
        595                 600                 605
Ala Cys Leu Leu Pro Lys Leu Asp Glu Leu Arg Asp Glu Gly Lys Ala
610                 615                 620
Ser Ser Ala Lys Gln Arg Leu Lys Cys Ala Ser Leu Gln Lys Phe Gly
625                 630                 635                 640
Glu Arg Ala Phe Lys Ala Trp Ala Val Ala Arg Leu Ser Gln Arg Phe
                645                 650                 655
Pro Lys Ala Glu Phe Ala Glu Val Ser Lys Leu Val Thr Asp Leu Thr
            660                 665                 670
Lys Val His Thr Glu Cys Cys His Gly Asp Leu Leu Glu Cys Ala Asp
        675                 680                 685
Asp Arg Ala Asp Leu Ala Lys Tyr Ile Cys Glu Asn Gln Asp Ser Ile
690                 695                 700
Ser Ser Lys Leu Lys Glu Cys Cys Glu Lys Pro Leu Leu Glu Lys Ser
705                 710                 715                 720
His Cys Ile Ala Glu Val Glu Asn Asp Glu Met Pro Ala Asp Leu Pro
                725                 730                 735
Ser Leu Ala Ala Asp Phe Val Glu Ser Lys Asp Val Cys Lys Asn Tyr
            740                 745                 750
Ala Glu Ala Lys Asp Val Phe Leu Gly Met Phe Leu Tyr Glu Tyr Ala
        755                 760                 765
Arg Arg His Pro Asp Tyr Ser Val Val Leu Leu Leu Arg Leu Ala Lys
770                 775                 780
Thr Tyr Glu Thr Thr Leu Glu Lys Cys Cys Ala Ala Ala Asp Pro His
785                 790                 795                 800
Glu Cys Tyr Ala Lys Val Phe Asp Glu Phe Lys Pro Leu Val Glu Glu
                805                 810                 815
Pro Gln Asn Leu Ile Lys Gln Asn Cys Glu Leu Phe Glu Gln Leu Gly
            820                 825                 830
Glu Tyr Lys Phe Gln Asn Ala Leu Leu Val Arg Tyr Thr Lys Lys Val
        835                 840                 845
Pro Gln Val Ser Thr Pro Thr Leu Val Glu Val Ser Arg Asn Leu Gly
850                 855                 860
Lys Val Gly Ser Lys Cys Cys Lys His Pro Glu Ala Lys Arg Met Pro
```

-continued

```
865                 870                 875                 880
Cys Ala Glu Asp Tyr Leu Ser Val Val Leu Asn Gln Leu Cys Val Leu
            885                         890                 895

His Glu Lys Thr Pro Val Ser Asp Arg Val Thr Lys Cys Cys Thr Glu
            900                 905                 910

Ser Leu Val Asn Arg Arg Pro Cys Phe Ser Ala Leu Glu Val Asp Glu
            915                 920                 925

Thr Tyr Val Pro Lys Glu Phe Asn Ala Glu Thr Phe Thr Phe His Ala
        930                 935                 940

Asp Ile Cys Thr Leu Ser Glu Lys Glu Arg Gln Ile Lys Lys Gln Thr
945                 950                 955                 960

Ala Leu Val Glu Leu Val Lys His Lys Pro Lys Ala Thr Lys Glu Gln
                965                 970                 975

Leu Lys Ala Val Met Asp Asp Phe Ala Ala Phe Val Glu Lys Cys Cys
                980                 985                 990

Lys Ala Asp Asp Lys Glu Thr Cys  Phe Ala Glu Glu Gly Lys Lys Leu
            995                 1000                1005

Val Ala  Ala Ser Gln Ala Ala  Leu Gly Leu
    1010                 1015
```